(12) United States Patent
Ide et al.

(10) Patent No.: US 11,298,274 B2
(45) Date of Patent: Apr. 12, 2022

(54) UNDERPANTS-TYPE DISPOSABLE DIAPER

(71) Applicant: Daio Paper Corporation, Ehime (JP)

(72) Inventors: Aya Ide, Ehime (JP); Yoshitake Ishikawa, Ehime (JP); Yosuke Mori, Ehime (JP)

(73) Assignee: Daio Paper Corporation, Ehime (JP)

( * ) Notice: Subject to any disclaimer, the term of this patent is extended or adjusted under 35 U.S.C. 154(b) by 470 days.

(21) Appl. No.: 16/337,659

(22) PCT Filed: Oct. 16, 2017

(86) PCT No.: PCT/JP2017/037310
§ 371 (c)(1),
(2) Date: Mar. 28, 2019

(87) PCT Pub. No.: WO2018/074396
PCT Pub. Date: Apr. 26, 2018

(65) Prior Publication Data
US 2019/0231614 A1    Aug. 1, 2019

(30) Foreign Application Priority Data
Oct. 21, 2016 (JP) ................. 2016-206860

(51) Int. Cl.
*A61F 13/514* (2006.01)
*A61F 13/496* (2006.01)
(Continued)

(52) U.S. Cl.
CPC .......... *A61F 13/5146* (2013.01); *A61F 13/49* (2013.01); *A61F 13/494* (2013.01);
(Continued)

(58) Field of Classification Search
CPC ........ A61F 13/49; A61F 13/494; A61F 13/51; A61F 13/511; A61F 13/5146;
(Continued)

(56) References Cited

U.S. PATENT DOCUMENTS 5,766,212 A * 6/1998 Jitoe ................. A61F 13/42
604/361
7,189,301 B2    3/2007 Ostubo et al.
(Continued)

FOREIGN PATENT DOCUMENTS

| CN | 208756331 | 4/2019 |
| EP | 1626690 | 12/2004 |

(Continued)

OTHER PUBLICATIONS

International Search Report, PCT/JP2017/037310, dated Jan. 16, 2018.

*Primary Examiner* — Michele M Kidwell
(74) *Attorney, Agent, or Firm* — Andrus Intellectual Property Law, LLP

(57) ABSTRACT

An underpants-type disposable diaper has a display sheet containing a resin film between an inner member and at least one of a front side outer member and a back side outer member. A cover nonwoven fabric is provided with a plurality of holes having intervals and penetrating a front and a back is interposed from at least a crotch side edge of an outer member overlapping the display sheet to a side of a waist opening between the display sheet and a liquid impervious sheet. An internal surface and an external surface of the cover nonwoven fabric are bonded to facing surfaces, respectively, through a hot melt adhesive. Compatibility between prevention of deterioration of appearance of the display sheet and prevention of a decrease in air permeability is achieved.

7 Claims, 24 Drawing Sheets

(51) Int. Cl.
*A61F 13/511* (2006.01)
*A61F 13/49* (2006.01)
*A61F 13/515* (2006.01)
*A61F 13/494* (2006.01)
*A61F 13/535* (2006.01)
*A61F 13/84* (2006.01)
*A61F 13/56* (2006.01)
*A61F 13/51* (2006.01)

(52) U.S. Cl.
CPC ...... *A61F 13/496* (2013.01); *A61F 13/49014* (2013.01); *A61F 13/51* (2013.01); *A61F 13/511* (2013.01); *A61F 13/515* (2013.01); *A61F 13/5116* (2013.01); *A61F 13/51496* (2013.01); *A61F 13/535* (2013.01); *A61F 13/56* (2013.01); *A61F 13/84* (2013.01); *A61F 2013/49093* (2013.01)

(58) Field of Classification Search
CPC .. A61F 13/51496; A61F 13/535; A61F 13/56; A61F 13/84
See application file for complete search history.

(56) References Cited

U.S. PATENT DOCUMENTS

| | | | | |
|---|---|---|---|---|
| 2004/0167494 | A1* | 8/2004 | Otsubo | A61F 13/49011 604/385.27 |
| 2004/0230171 | A1* | 11/2004 | Ando | A61F 13/49011 604/355 |
| 2005/0131374 | A1* | 6/2005 | Otsubo | A61F 13/496 604/385.27 |
| 2006/0030831 | A1 | 2/2006 | Matsuda et al. | |
| 2012/0157948 | A1* | 6/2012 | Nhan | A61F 13/42 604/361 |
| 2012/0283682 | A1* | 11/2012 | Otsubo | A61F 13/49009 604/385.01 |
| 2019/0231614 | A1 | 8/2019 | Ide et al. | |
| 2020/0315866 | A1* | 10/2020 | Fukae | A61F 13/5148 |

FOREIGN PATENT DOCUMENTS

| | | |
|---|---|---|
| JP | 2004-73428 | 3/2004 |
| JP | 2005-245789 | 9/2005 |
| JP | 2006-525857 | 11/2006 |
| JP | 2010-5342 | 1/2010 |
| JP | 2011-515593 | 5/2011 |
| JP | 2011-147516 | 8/2011 |
| JP | 4964993 | 4/2012 |
| JP | 2012-100694 | 5/2012 |
| JP | 2014-28308 | 2/2014 |
| JP | 2015-186563 | 10/2015 |
| JP | 2018-064869 | 4/2018 |

* cited by examiner (a)

(b)

(c)

(a)

(b)　　　　　　　(c)

(a)

(b)

(c)

(a)

(b)

(c)

(a)

(b)

UNDERPANTS-TYPE DISPOSABLE DIAPER

CROSS-REFERENCE TO RELATED APPLICATIONS

This application is the U.S. national stage application of International Application PCT/JP2017/037310, filed Oct. 16, 2017, which international application was published on Apr. 26, 2018, as International Publication WO 2018/074396 in the Japanese language. The International Application claims priority of Japanese Patent Application No. 2016-206860, filed Oct. 21, 2016. The international application and Japanese application are both incorporated herein by reference, in entirety.

TECHNICAL FIELD

The present invention relates to an underpants-type disposable diaper.

BACKGROUND ART

In general, an underpants-type disposable diaper includes an outer member for individually or integrally configuring a front body and a back body and an inner member having an absorbent body attached to the outer member to extend from the front body to the back body, and a waist opening and a pair of left and right leg openings are formed by joining both side edge portions of the outer member of the front body and both side edge portions of the outer member of the back body to form side seal portions.

In such an underpants-type disposable diaper, to improve fitting to a body, the outer member is configured to have a stacked structure including a plurality of sheet layers, and various elastic members are attached between the sheet layers in a stretched state. Especially, a diaper, in which elongated elastic members extending along a width direction are attached in a stretched state in the width direction with intervals in a front-back direction in lower torsos defined as front-back direction zones corresponding to side seal portions and an intermediate region located between front and back lower torsos, has relatively high fitting with respect to the body (for example, see Patent Literatures 1 to 5).

The lower torsos and the intermediate region overlap the front-back direction zones having the absorbent body, and internal and external fixing portions for fixing the inner member to the outer member are present in the zones. Therefore, even when the elastic members are provided to traverse the front-back direction zones having the absorbent body, a stretching/contracting function thereof is limited by the rigidity of the absorbent body. In addition, there is concern that the absorbent body may contract in the width direction to degrade wearing feeling or appearance, or distortion or cracking of the absorbent body may occur to decrease absorption performance.

For this reason, in general, there has been conventionally adopted a scheme of continuously attaching elastic members along the width direction and finely cutting almost the entire part overlapping the absorbent body, or a scheme of not fixing an elastic member to the outer member in a part overlapping the absorbent body and cutting the part at one place in the middle in the width direction, thereby forming a non-stretchable region in which a contraction force in the width direction does not act on the absorbent body. As this cutting scheme, as a scheme in which holes are not formed in an inner sheet layer and an outer sheet layer covering an inside and an outside of the elastic member, a scheme of cutting the elastic member in a state of interposing the elastic member between the inner sheet layer and the outer sheet layer by pressing and heating a cut site from the inside and the outside thereof has been known.

On the other hand, a contraction force of the elastic member hardly acts and contraction wrinkles are rarely formed on the non-stretchable region of the outer member, and thus the non-stretchable region is excellent in light permeability when compared to a part in which contraction wrinkles are formed. Therefore, a display sheet having a pattern, etc. has been interposed between sheet layers of the outer member in the non-stretchable region (see Patent Literature 2) or between the outer member and the inner member (see Patent Literature 3). As a material of such a display sheet, a resin film has been suitably used from viewpoints of being inexpensive and enabling high-definition printing.

Here, in the case of interposing the display sheet between the sheet layers of the outer member, in a state in which the elastic member and the display sheet are disposed between the outer sheet layer and the inner sheet layer, the elastic member is cut by pressing and heating in a region having the display sheet to form the non-stretchable region. Thus, when the display sheet is formed of the resin film, there is concern that traces having concavo-convex figures may remain in the display sheet in the cut site of the elastic member, holes may be formed by tearing or melting, and thus these cutting traces may degrade the appearance of the display sheet.

Meanwhile, a mode in which the display sheet is interposed between the outer member and the inner member may be a particularly preferably mode in a case in which the resin film is used as the material of the display sheet since a process of cutting the elastic member for forming the non-stretchable region at the time of manufacture may be performed in a state of not having the display sheet.

However, the liquid impervious sheet made of the resin film is exposed in most of a region overlapping the display sheet on a back surface of the inner member. Further, when the display sheet is bonded to this portion through a hot melt adhesive, two resin films are directly bonded, and thus there is a problem that air permeability is lowered.

CITATION LIST

Patent Literature

Patent Literature 1: JP 2004-073428 A
Patent Literature 2: JP 2006-525857 A
Patent Literature 3: JP 2011-147516 A
Patent Literature 4: JP 2014-028308 A
Patent Literature 5: JP 4964993 B1

SUMMARY OF INVENTION

Technical Problem

Therefore, a main problem of the invention is to achieve compatibility between prevention of deterioration of appearance of a display sheet and prevention of a decrease in air permeability in the case of using a resin film as a material of the display sheet.

Solution to Problem

Representative aspects of the invention solving the above-mentioned problems are as follows.

<First Aspect>

An underpants-type disposable diaper comprising: a front side outer member configuring at least a lower torso portion of a front body and a back side outer member configuring at least a lower torso portion of a back body, the front side outer member and the back side outer member being separated from each other and spaced apart in a front-back direction in a middle in the front-back direction;

an inner member including a liquid pervious top sheet located on a front surface side, a liquid impervious sheet formed of a resin film located on a back surface side, and an absorbent body interposed therebetween, extending in the front-back direction from the front side outer member to the back side outer member and being joined to each of the front side outer member and the back side outer member, a waist opening and a pair of left and right leg openings being formed by joining both side portions of the front side outer member and both side portions of the back side outer member, respectively; and a display sheet formed of a resin film and being provided between at least one of the front side outer member and the back side outer member and the inner member, in which a perforated nonwoven fabric provided with a plurality of holes having intervals and penetrating a front and a back is interposed at least from a crotch side edge of the outer member overlapping the display sheet, toward a side of the waist opening, to a region between the display sheet and the liquid impervious sheet, and an internal surface and an external surface of the perforated nonwoven fabric are bonded to facing surfaces, respectively, through a hot melt adhesive.

(Effects)

In this aspect, a mode in which the display sheet is interposed between the outer member and the inner member is adopted, and a process of cutting the elastic member for forming the non-stretchable region can be performed without the display sheet at the time of manufacture. Thus, it is possible to prevent deterioration of appearance of the display sheet. In addition, since the perforated nonwoven fabric extends at least from the crotch side edge of the outer member a region between the display sheet and the liquid impervious sheet on the waist opening side, and air can permeate through the inside of the perforated nonwoven fabric from the outside of the disposable diaper and to the region between the display sheet and the liquid impervious sheet, it is possible to prevent the deterioration of the air permeability when the resin film is used as the material of the display sheet.

<Second Aspect>

The underpants-type disposable diaper according to the first aspect, in which the perforated nonwoven fabric is a cover nonwoven fabric which extends from a region between the front side outer member and the inner member to a region between the back side outer member and the inner member and covers a back surface of the inner member in a site in which the front side outer member and the back side outer member are spaced apart.

(Effects)

In an outer member separated type underpants-type disposable diaper in which the front side outer member and the back side outer member are spaced apart in the front-back direction, the inner member is exposed between the front side outer member and the back side outer member, and thus it is known to cover the back surface of the inner member with the cover nonwoven fabric so that the liquid impervious sheet is not exposed on the back surface of the inner member. This aspect is used both as the cover nonwoven fabric that covers the back surface of the inner member and the perforated nonwoven fabric disposed between the display sheet and the liquid impervious sheet, and a single perforated nonwoven fabric can cover the back surface of the inner member and improve air permeability of a part having the display sheet.

<Third Aspect>

The underpants-type disposable diaper according to the second aspect, further comprising side gathers extending from both side portions of the inner member to come into contact with peripheries of legs of a wearer, wherein each of the side gathers has a base at a side portion of the inner member on a back surface side of the liquid impervious sheet and has a gather nonwoven fabric forming an external surface at least from the base to a tip, and the perforated nonwoven fabric extends from a region between a base portion of at least one of the side gathers and the liquid impervious sheet to a region between a base portion of the other one of the side gathers and the liquid impervious sheet.

(Effects)

Since the both side portions of the perforated nonwoven fabric are covered with the gather nonwoven fabric, the both side portions of the perforated nonwoven fabric are rarely peeled off from the liquid impervious sheet.

<Fourth Aspect>

The underpants-type disposable diaper according to any one of the first to third aspects, in which an inner and outer joined portion that joins the inner member and the outer member overlapping the perforated nonwoven fabric is provided over a region overlapping the perforated nonwoven fabric and a region on both width-direction sides beyond the overlapping region.

(Effects)

In this case, it is possible to firmly fix the both side portions of the perforated nonwoven fabric, and the both side portions of the perforated nonwoven fabric are rarely peeled off from the inner member.

<Fifth Aspect>

The underpants-type disposable diaper according to any one of the first to fourth aspects, in which the hot melt adhesive is not present on a center side of a peripheral edge portion of a region overlapping the holes, and the hot melt adhesive is applied in a continuous surface shape in a portion other than the peripheral edge portion of the region overlapping the holes, in a bonded region of at least one of the internal surface and the external surface of the perforated nonwoven fabric.

(Effects)

When such a bonding structure is adopted, the hot melt adhesive is not present on the center side of the peripheral edge portion in the region overlapping the holes, and thus air permeability is excellent. In addition, in a portion having such a bonding structure only on a surface opposite from a surface to be touched by the skin, a sticky texture due to the hot melt adhesive is rarely obtained, and the peripheral portion of the hole is reliably fixed to the facing surface. Since the peripheral edge portion of the region overlapping the hole is a portion close to the peripheral portion of the hole, even when the hot melt adhesive protrudes to this portion, the hot melt adhesive is rarely directly touched at the time of touching the surface on the opposite side from a bonded surface in the perforated nonwoven fabric with a hand.

<Sixth Aspect>

The underpants-type disposable diaper according to any one of the first to fourth aspects, in which a peripheral portion of the hole is formed into a warped portion warped to the side of the liquid impervious sheet in the perforated nonwoven fabric, at least a tip portion of the warped portion in the perforated nonwoven fabric has a bonded portion stuck to a facing surface on the side of the liquid impervious sheet through the hot melt adhesive, and a portion other than the bonded portion in the perforated nonwoven fabric is not bonded to the facing surface on the side of the liquid impervious sheet.

(Effects)

When such a bonding structure is adopted, the bonded area decreases, and thus flexibility is not impaired, and the peripheral portion of the hole is reliably fixed to the facing surface on the liquid impervious sheet side. In particular, the warped portion supports the perforated nonwoven fabric with respect to the facing surface on the liquid impervious sheet side as a post, and thus is bulky in comparison with a non-porous nonwoven fabric having the same basis weight, and is excellent in air permeability.

Advantageous Effects of Invention

As described above, the invention is advantageous in that it is possible to achieve compatibility between prevention of deterioration of appearance of a display sheet and prevention of a decrease in air permeability in the case of using a resin film as a material of the display sheet.

DESCRIPTION OF EMBODIMENTS

Figure 1:
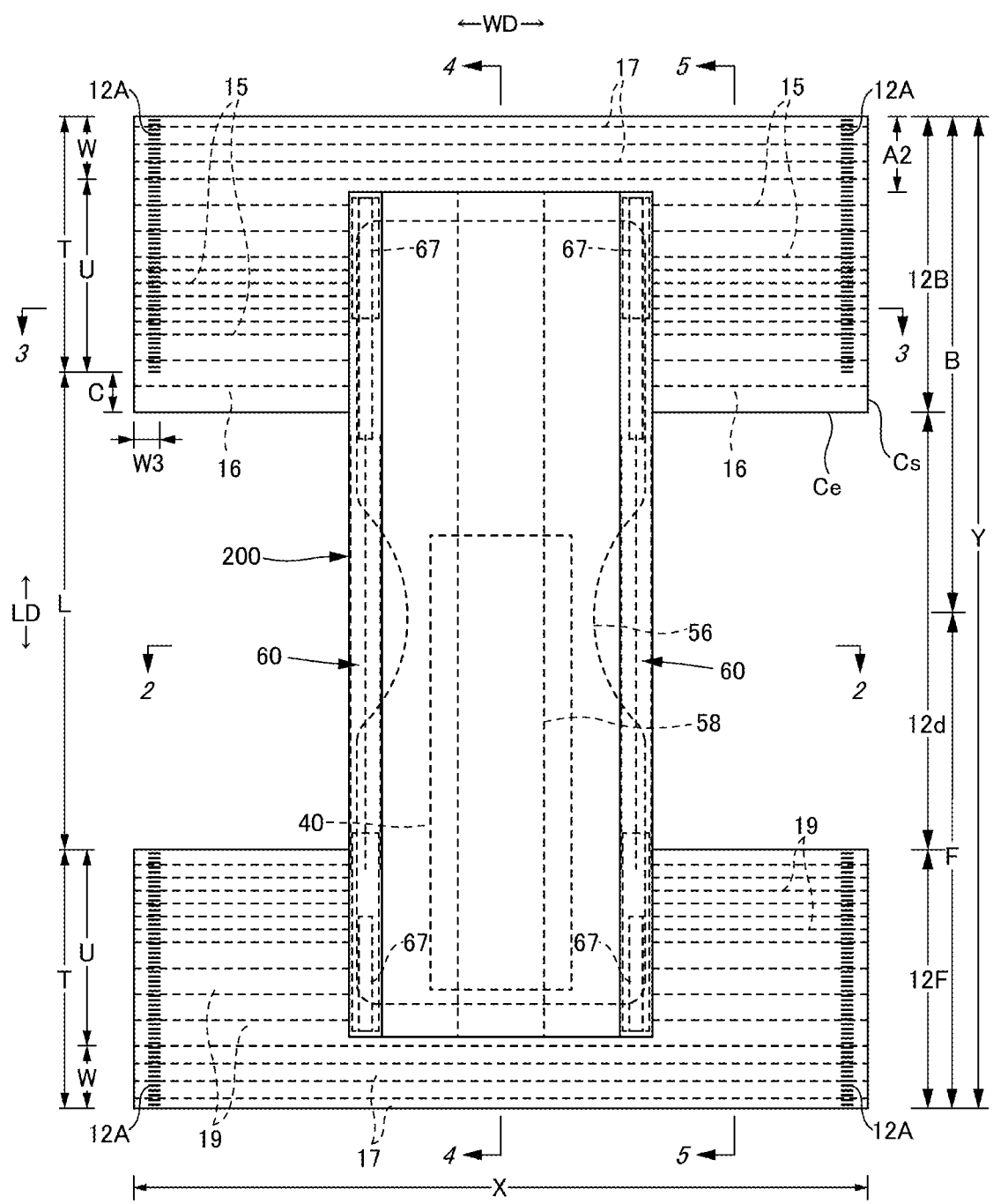
FIG. 1 is a plan view illustrating an internal surface of an underpants-type disposable diaper in a spread state.

Hereinafter, an embodiment of the invention will be described in detail with reference to accompanying drawings. A dotted pattern portion in a cross-sectional view illustrates an adhesive as bonding means for bonding respective constituent members located on a front surface side and a back surface side thereof, and is formed by solid coating, bead coating, curtain coating, summit coating, or spiral coating of a hot melt adhesive, pattern coating (transfer of a hot melt adhesive in a relief printing method), etc. Alternatively, a fixing part of the elastic member is formed by application of a hot melt adhesive to an outer circumferential surface using comb gun or sure-wrap application in place of or together with the above schemes. Examples of the hot melt adhesive include various types of adhesives such as EVA-based adhesive, adhesive rubber-based (elastomer-based), polyolefin-based, and polyester/polyamide-based adhesives, which can be used without particular limitation. As the bonding means for bonding the respective constituent members, it is possible to use means by material welding such as heat sealing or ultrasonic sealing.

FIG. 1 to FIG. 13 illustrate an example of an underpants-type disposable diaper. The underpants-type disposable diaper includes a front side outer member 12F forming at least a lower torso portion of a front body F, a back side outer member 12B forming at least a lower torso portion of a back body B, and an inner member 200 provided on an inner side of the outer members 12F and 12B to extend from the front side outer member 12F to the back side outer member 12B through a crotch portion. Both side portions of the front side outer member 12F and both side portions of the back side outer member 12B are joined to form side seal portions 12A, so that an opening formed by front and back end portions of the outer members 12F and 12B becomes a waist opening WO passing through a truck of a wearer, and portions surrounding by lower edges of the outer members 12F and 12B and a side edge of the inner member 200 at both sides of the inner member 200 in a width direction become leg openings LO passing through legs. The inner member 200 is a portion that absorbs and holds excrement such as urine and the outer members 12F and 12B are portions for supporting the inner member 200 with respect to a body of the wearer. In addition, a symbol Y indicates an entire length of the diaper in a spread state (a length in a front-back direction from the edge of the waist opening WO of the front body F to the edge of the waist opening WO of the back body B), and a symbol X indicates an entire width of the diaper in the spread state.

The underpants-type disposable diaper of this embodiment includes lower torsos T defined as front-back direction zones having the side seal portions 12A (front-back direction zones from the waist opening WO to upper ends of the leg openings LO) and an intermediate region L defined as a front-back direction zone of portions forming the leg openings LO (between a front-back direction region having the side seal portions 12A of the front body F and a front-back direction region having the side seal portions 12A of the back body B). Each of the lower torsos T can be divided into a "waist portion" W conceptually forming the edge portion of the waist opening and an "lower waist portion" U corresponding to a portion on a lower side thereof. Normally, when a boundary at which stretching stress in the width direction WD changes (for example, a fineness or a stretch rate of the elastic member changes) is included in the lower torso T, the waist opening WO side closest to the boundary is the waist portion W. When such a boundary is not present, a waist opening WO side of an absorbent body 56 or the inner member 200 is the waist portion W. Lengths thereof in the front-back direction vary depending on the size of the product and may be appropriately determined. For example, the waist portion W can be set to 15 to 40 mm, and a lower waist portion U can be set to 65 to 120 mm. Meanwhile, both side edges of the intermediate region L are narrowed in a U shape or a curved shape to follow circumferences of the legs of the wearer, and correspond to sites in which the legs of the wearer are put. As a result, the underpants-type disposable diaper in the spread state has a substantially hourglass shape as a whole.

(Inner Member)

Figure 3:
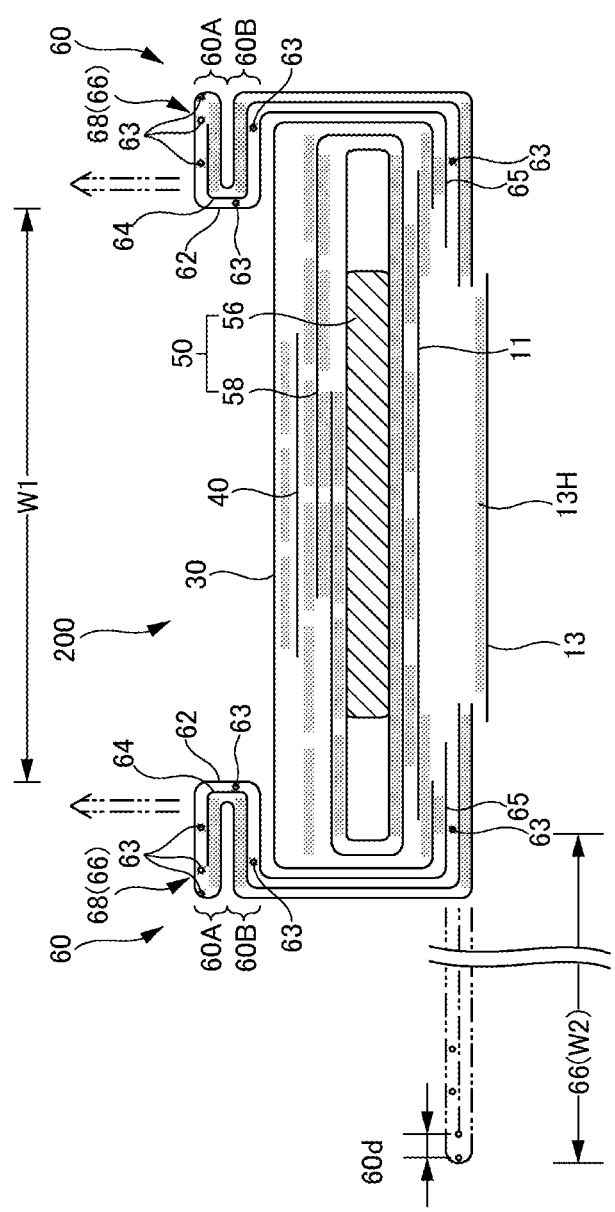
FIG. 3 is a cross-sectional view taken along 2-2 line of FIG. 1.
Figure 4:
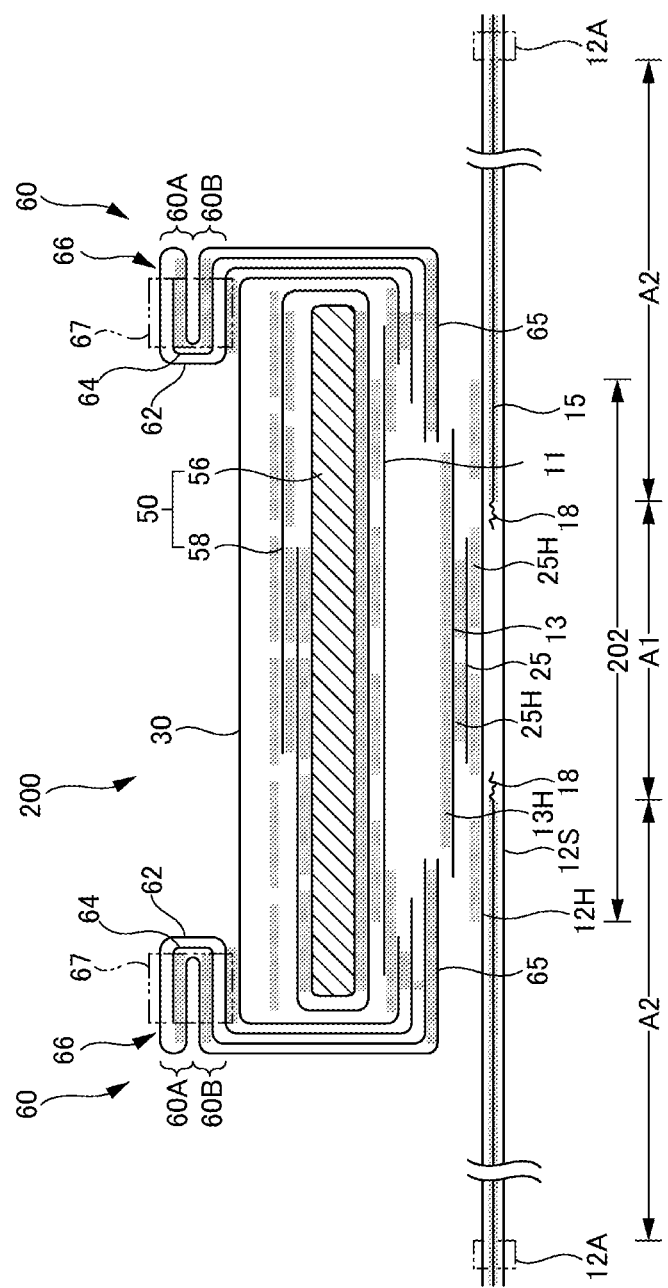
FIG. 4 is a cross-sectional view taken along 3-3 line of FIG. 1.
Figure 5:
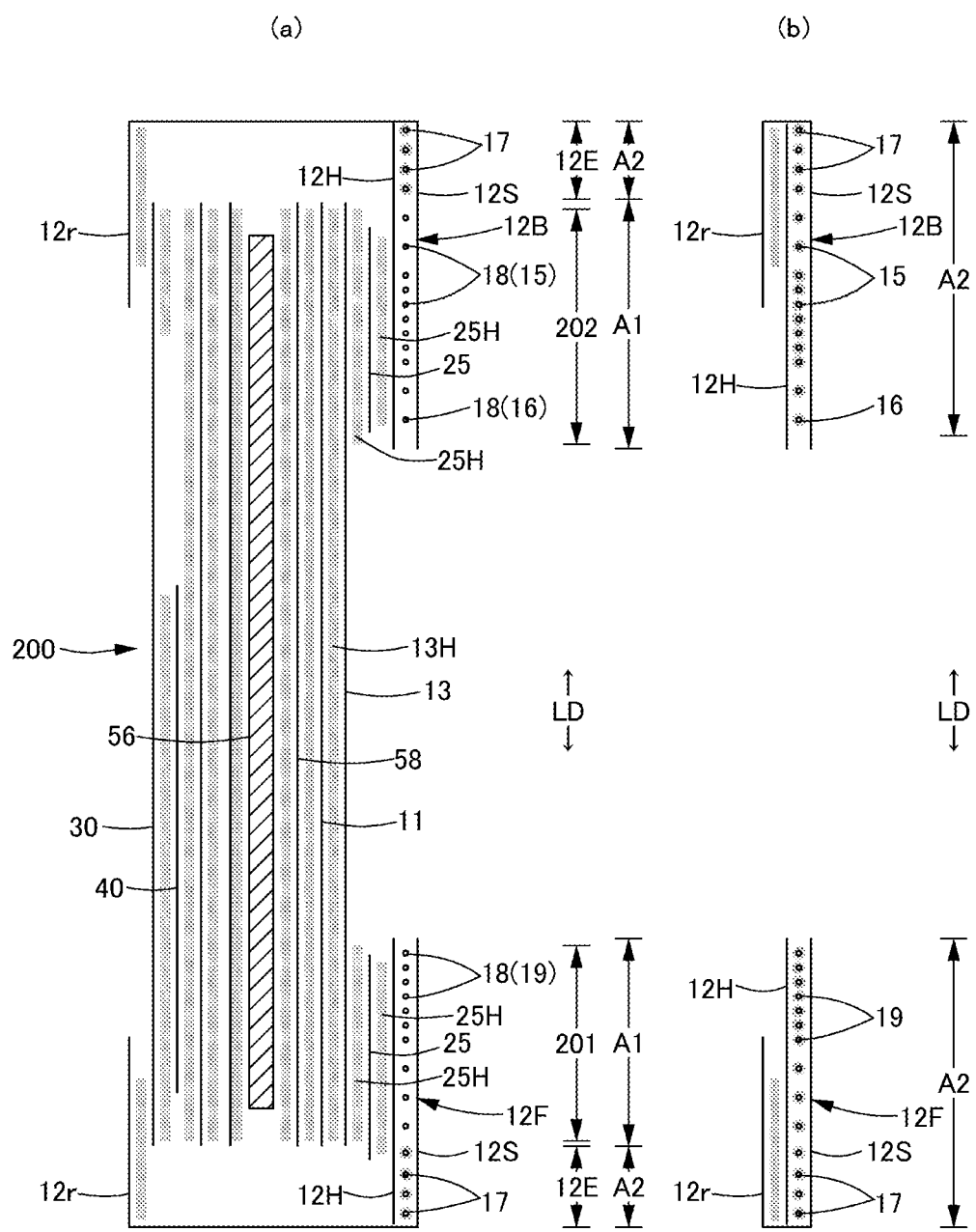
FIG. 5(a) is a cross-sectional view taken along 4-4 line of FIG. 1.
FIG. 5(b) is a cross-sectional view taken along 5-5 line of FIG. 1.
Figure 6:
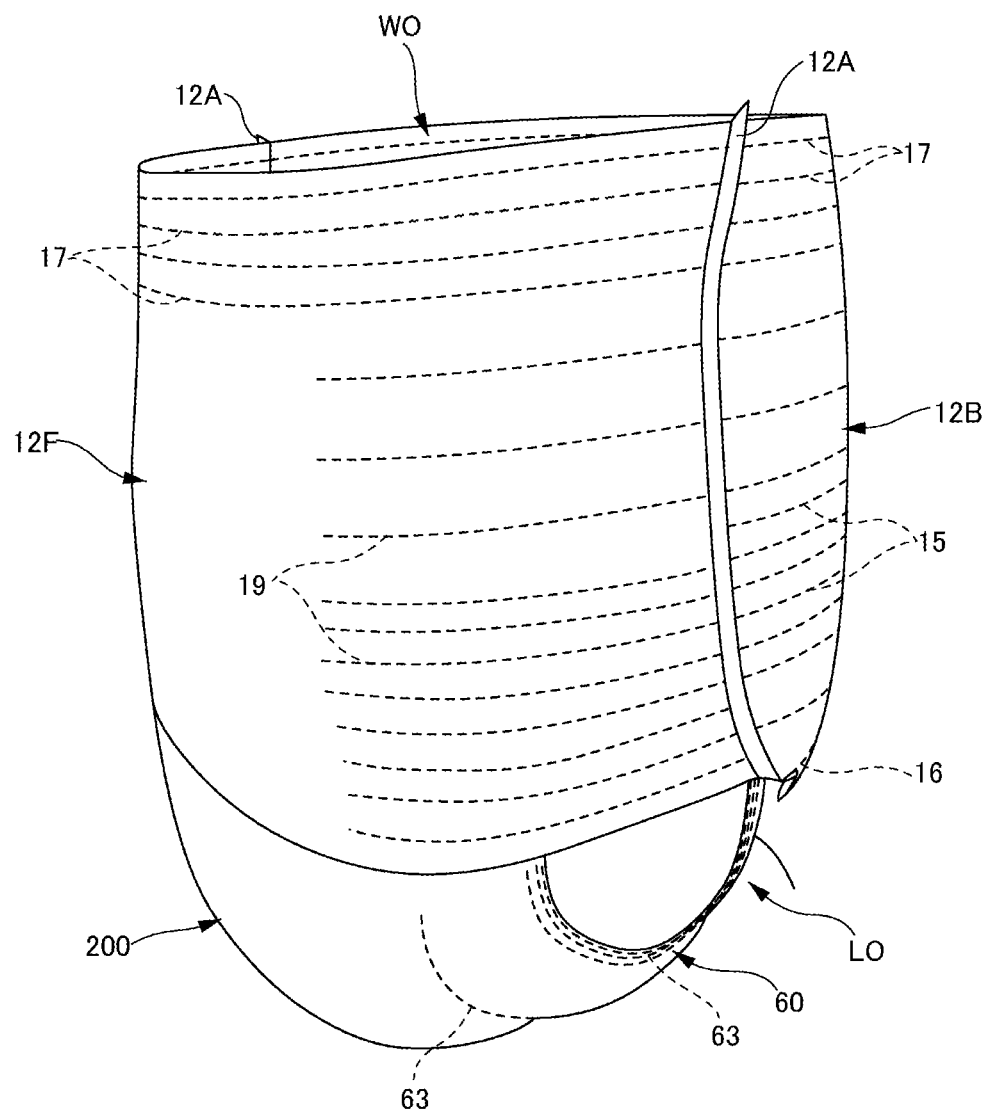
FIG. 6 is a perspective view of the underpants-type disposable diaper (holes are omitted).

An arbitrary shape can be adopted for the inner member 200. However, a rectangle is adopted in an illustrated embodiment. As illustrated in FIG. 3 to FIG. 5, the inner member 200 includes a top sheet 30 corresponding to a body side, a liquid impervious sheet 11, and an absorbent element 50 interposed therebetween, and is a main unit section responsible for an absorption function. Reference numeral 40 denotes an intermediate sheet (second sheet) provided between the top sheet 30 and the absorbent element 50 to promptly transfer a liquid permeating through the top sheet 30 to the absorbent element 50, and reference numeral 60 denotes side gathers 60 extending from both side portions of the inner member 200 to come into contact with a periphery of the legs of the wearer so as to prevent excrement from leaking to both sides of the inner member 200.

(Top Sheet)

The top sheet 30 has a property of permeating liquid, and examples thereof may include a perforated or nonporous nonwoven fabric, a porous plastic sheet, etc. In addition, a raw material fiber of the nonwoven fabric is not particularly restricted. Examples thereof may include a synthetic fiber such as a polyolefin synthetic fiber such as polyethylene, polypropylene, etc., a polyester synthetic fiber, a polyamide synthetic fiber, etc., a regenerated fiber such as rayon or cupra, a natural fiber such as cotton, or a mixed fiber, a composite fiber, etc. using two types or more thereof. Further, the nonwoven fabric may be manufactured by any process. Examples of a processing method may include a known method such as a spun lace method, a spun bond method, a thermal bond method, a melt blown method, a needle-punch method, an air-through method, a point bond method, etc. For example, when flexibility and drapeability are required, the spun bond method and the spun lace method are preferable processing schemes. Further, when bulkiness and softness are required, the air-through method, the point bond method, and the thermal bond method are preferable processing schemes.

In addition, the top sheet 30 may be made of one sheet or a stacked sheet obtained by bonding two or more sheets. Similarly, the top sheet 30 may be made of one sheet or two or more sheets in a plane direction.

Both side portions of the top sheet 30 may be folded back to the back surface side at side edges of the absorbent element 50 or may laterally protrude beyond the side edges of the absorbent element 50 without folding back.

For the purpose of preventing positional shift with respect to the back surface side member, etc., it is desirable that the top sheet 30 is fixed to a member adjacent to the back surface side by bonding means based on material welding such as heat sealing or ultrasonic sealing or a hot melt adhesive. In the illustrated embodiment, the top sheet 30 is fixed to a surface of the intermediate sheet 40 and a surface of a portion of a package sheet 58 located on the front surface side of the absorbent body 56 by a hot melt adhesive applied to the back surface thereof.

(Intermediate Sheet)

To rapidly transfer the liquid permeating through the top sheet 30 to the absorbent body, it is possible to provide an intermediate sheet (also referred to as a "second sheet") 40 having a higher liquid permeation rate than that of the top sheet 30. The intermediate sheet 40 serves to rapidly transfer the liquid to the absorbent body to enhance an absorption performance of the absorbent body, and to prevent a "backflow" phenomenon of the absorbed liquid from the absorbent body. The intermediate sheet 40 can be omitted.

Examples of the intermediate sheet 40 may include a similar material to that of the top sheet 30, spun lace, spun bond, SMS, pulp nonwoven fabric, a mixed sheet of pulp and rayon, point bond or crepe paper. In particular, air-through nonwoven fabric is bulky, and thus is preferable. It is preferable to use a composite fiber having a core-sheath structure for the air-through nonwoven fabric. In this case, a resin used for a core may be polypropylene (PP). However, polyester (PET) having high rigidity is preferable. A basis weight is preferably 17 to 80 $g/m^2$, more preferably 25 to 60 $g/m^2$. A thickness of a raw material fiber of the nonwoven fabric is preferably 2.0 to 10 dtex. In order to increase the bulkiness of the nonwoven fabric, it is preferable to use an eccentric fiber having no core in a center, a hollow fiber, and an eccentric and hollow fiber as a mixed fiber of a whole or a part of the raw material fiber.

The intermediate sheet 40 of the illustrated embodiment is shorter than a width of the absorbent body 56 and disposed at a center. However, the intermediate sheet 40 may be provided over the whole width. A length of the intermediate sheet 40 in the front-back direction may be equal to the entire length of the diaper, equal to a length of the absorbent element 50 or within a short length range centered on a region in which a liquid is received.

For the purpose of preventing positional shift with respect to the back surface side member, etc., it is desirable that the intermediate sheet 40 is fixed to a member adjacent to the back surface side by bonding means based on material welding such as heat sealing or ultrasonic sealing or a hot melt adhesive. In the illustrated embodiment, the intermediate sheet 40 is fixed to a surface of a portion of the package sheet 58 located on the front surface side of the absorbent body 56 by a hot melt adhesive applied to the back surface thereof.

(Liquid Impervious Sheet)

A material of the liquid impervious sheet 11 is not particularly limited. However, examples thereof may include a plastic film made of a polyolefin resin such as polyethylene, polypropylene, etc., a laminated nonwoven fabric having a plastic film provided on a surface of a nonwoven fabric, a stacked sheet in which a nonwoven fabric, etc. is overlapped with and joined to a plastic film, etc. A material having liquid impermeability and moisture permeability which has been favorably used from the viewpoint of prevention of unevenness is preferably used for the liquid impervious sheet 11. A microporous plastic film obtained by kneading an inorganic filler in a polyolefin-based resin such as polyethylene or polypropylene, molding a sheet, and then performing stretching in a monoaxial or biaxial direction is widely used as the plastic film having moisture permeability. In addition, a nonwoven fabric using a micro-denier fiber, and a liquid impervious sheet obtained without using the plastic film by a method such as strengthening a leakage prevention property by reducing gaps of fibers by applying heat or pressure, use of a super absorbent resin or a hydrophobic resin, and coating of a water repellent agent may be used as the liquid impervious sheet 11. However, it is desirable to use a resin film to obtain sufficient bonding strength at the time of bonding to a cover nonwoven fabric 13 described below via a hot melt adhesive.

As illustrated in the figure, the liquid impervious sheet 11 has a width that fits on the back surface side of the absorbent element 50. In addition, to enhance a leakage prevention property, both sides of the absorbent element 50 may be wrapped to extend to both side portions of a surface of the absorbent element 50 on the top sheet 30 side. It is appropriate that a width of this extended portion is about 5 to 20 mm on both left and right sides.

In addition, an excretion indicator whose color changes due to absorption of a liquid component can be provided inside the liquid impervious sheet 11, particularly on the side of the absorbent body 56.

(Side Gathers)

The side gathers 60 extend along the both side portions of the inner member 200 over the whole in a front-back direction LD and are provided to prevent side leak by coming into contact with the peripheries of the legs of the wearer. In general, the side gathers 60 includes gathers referred to as three-dimensional gathers or gathers referred to as planar gathers.

The side gathers 60 of the first embodiment illustrated in FIG. 1, FIG. 3, and FIG. 4 are so-called three-dimensional gathers, and stand from side portions of the inner member 200 to the front surface side. In the side gathers 60, root side parts 60B obliquely stand toward a center side in the width direction, and tip side parts 60A with respect to an intermediate portion obliquely stand outward in the width direction. However, the invention is not limited thereto. As in a second embodiment described below, the embodiment may be appropriately changed to an embodiment in which the parts stand to the center side in the width direction as a whole.

More specifically, the side gathers 60 of the first embodiment are obtained by folding back belt-shaped gather nonwoven fabrics 62 having an equal length to a front-back direction length of the inner member 200 in the width direction WD in two parts at a portion corresponding to a tip, and fixing a plurality of elongated gather elastic members 63 with intervals in the width direction WD in a stretched state along a longitudinal direction between a folded portion and a sheet in the vicinity thereof. In the side gathers 60, a base portion located on an opposite side from a tip portion (an end portion on an opposite side from the sheet folded portion in the width direction WD) is set as a root portion 65 fixed to a side portion on a back surface side of the liquid impervious sheet 11 in the inner member 200, and a portion other than the root portion 65 is set as a main unit portion 66 (a portion on a side of the folded portion) extending from the root portion 65. In addition, the main unit portion 66 includes a root side part 60B extending to the center side in the width direction and a tip side part 60A folded back at a tip of the root side part 60B to extend outward in the width direction. This embodiment corresponds to side gathers 60 of a surface contact type. However, it is possible to adopt side gathers 60 of a line contact type which are not folded back outward in the width direction. Further, in the main unit portion 66, both end portions in the front-back direction are set as fallen parts 67 fixed to side surfaces of the top sheet 30 in a fallen state, and an intermediate portion in the front-back direction located therebetween is set as a free part 68 which is not fixed. The gather elastic members 63 extending along the front-back direction LD are fixed to at least a tip portion of the free part 68 in a stretched state.

In the side gathers 60 of the first embodiment configured as described above, a contraction force of the gather elastic members 63 acts so that the both end portions in the front-back direction approach to each other. However, since the both end portions in the front-back direction in the main unit portion 66 are fixed not to stand, and a part therebetween is set as the free part 68 which is not fixed, only the free part 68 stands to come into contact with the body side as illustrated in FIG. 3. In particular, when the root portion 65 is located on the back surface side of the inner member 200, the free part 68 stands to open outward in the width direction in the crotch portion and the vicinity thereof. Thus, the side gathers 60 come into surface contact with the peripheries of the legs, and fitting is improved.

In a bending mode in which the main unit portion 66 includes the root side part 60B extending to the center side in the width direction and the tip side part 60A folded back at the tip of the root side part 60B to extend outward in the width direction as in the side gathers 60 of the first embodiment, the tip side part 60A and the root side part 60B are bonded together in a fallen state in the fallen part 67, and the root side part 60B is bonded to the top sheet 30 in a fallen state. For bonding facing surfaces in the fallen part 67, it is possible to use at least one of a hot melt adhesive based on various coating methods and means based on material welding such as heat sealing, ultrasonic sealing, etc. In this case, bonding between the root side part 60B and the top sheet 30 and bonding between the tip side part 60A and the root side part 60B may be performed by the same means or different means. For example, in a preferable embodiment, bonding between the root side part 60B and the top sheet 30 is performed by the hot melt adhesive, and bonding between the tip side part 60A and the root side part 60B is performed by material welding.

Figure 10:
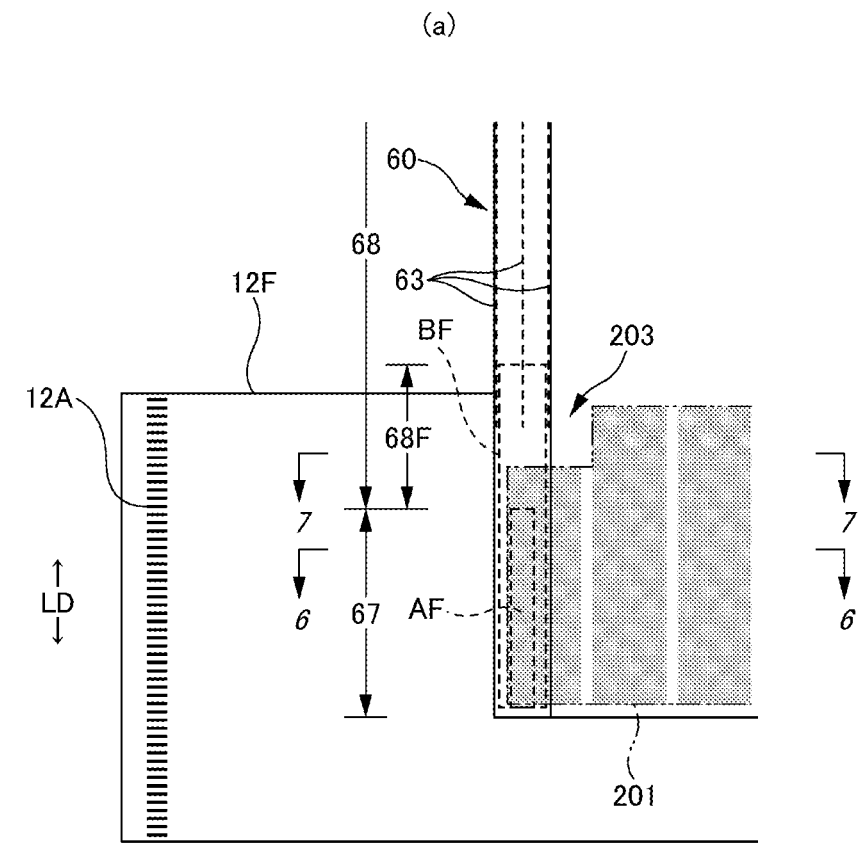
FIG. 10(a) is a plan view illustrating a main part of a front side of the underpants-type disposable diaper in the spread state.
FIG. 10(b) is a cross-sectional view taken along 6-6 line.
FIG. 10(c) is a cross-sectional view taken along 7-7 line.
Figure 10:
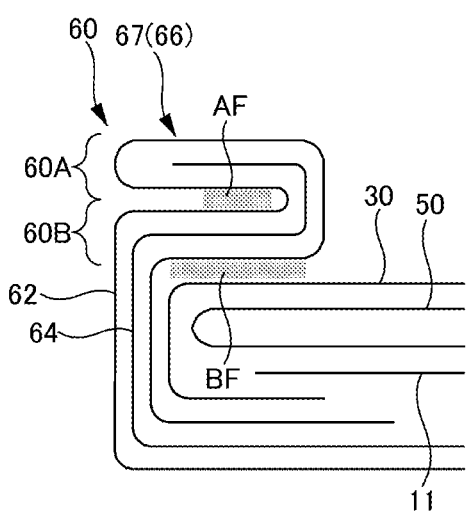
Figure 10:
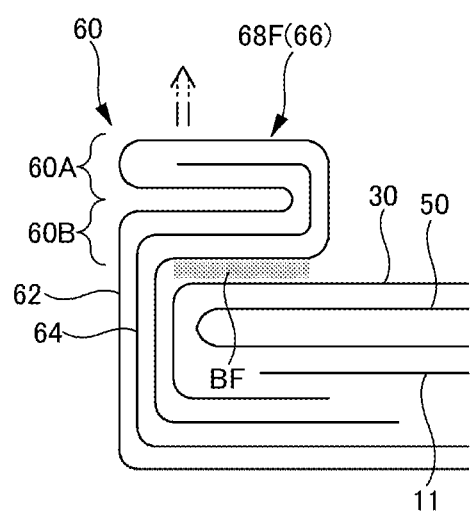

In particular, in an outer member separated type underpants-type disposable diaper in which the front side outer member 12F and the back side outer member 12B are spaced apart in the front-back direction LD, as illustrated in FIG. 10, it is preferable to provide a front side half fallen part 68F in which the root side part 60B is bonded to the top sheet 30 in a fallen state continuously or adjacent to a back side of a front side fallen part 67, and the tip side part 60A and the root side part 60B are not bonded together. In the front side half fallen part 68F, only the tip side part 60A is free. Thus, even though a height is low, the tip portion reliably rises with respect to the top sheet 30 by contraction of the gather elastic member 63. Therefore, fitting of the side gather 60 is excellent for an inguinal region in which a gap is likely to be generated. In addition, in this case, it is more preferable that the front side half fallen part 68F is the same as a back edge of the front side outer member 12F or extends to the center side in the front-back direction therefrom (that is, the front side half fallen part 68F includes an intersection position of the front side outer member 12F and the inner member 200). In a normal case, it is preferable that a length of the front side fallen part 67 in the front-back direction is about 0.10 to 0.25 times a length of the inner member 200 in the front-back direction, and a dimension obtained by adding a length of the front side half fallen part 68F in the front-back direction thereto is about 0.15 to 0.30 times the length of the inner member 200 in the front-back direction. In FIG. 10, reference symbol AF denotes the hot melt adhesive that bonds the tip side part 60A and the root side part 60B, and reference symbol BF denotes the hot melt adhesive that bonds the root side part 60B and the top sheet 30.

Figure 11:
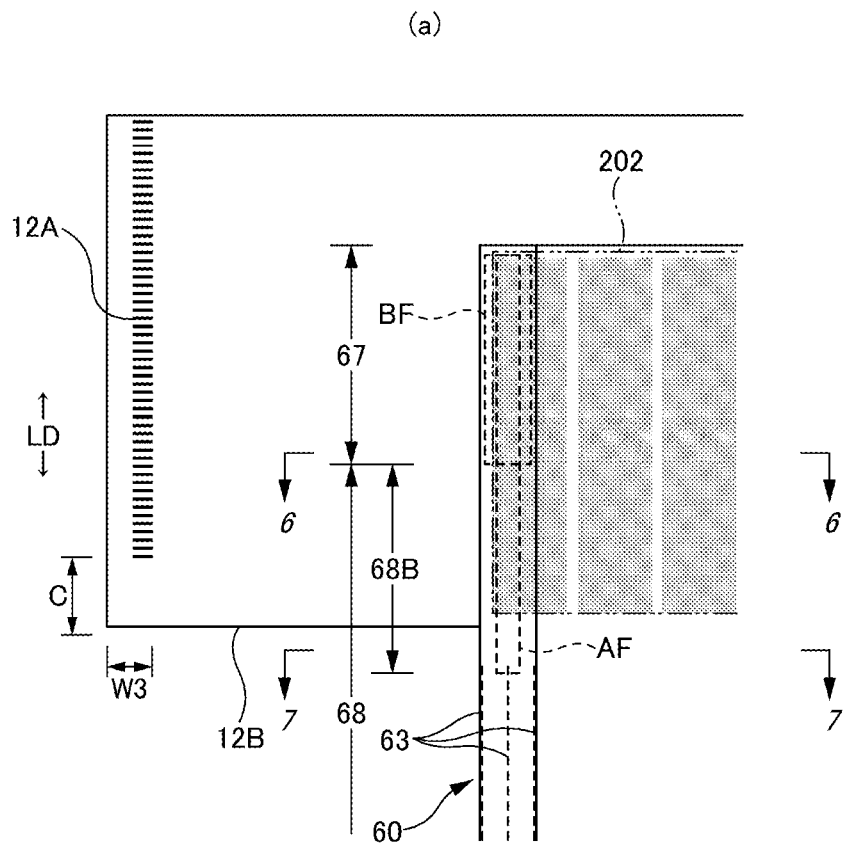
FIG. 11(a) is a plan view illustrating a main part of a back side of the underpants-type disposable diaper in the spread state.
FIG. 11(b) is a cross-sectional view taken along 6-6 line.
FIG. 11(c) is a cross-sectional view taken along 7-7 line.
Figure 11:
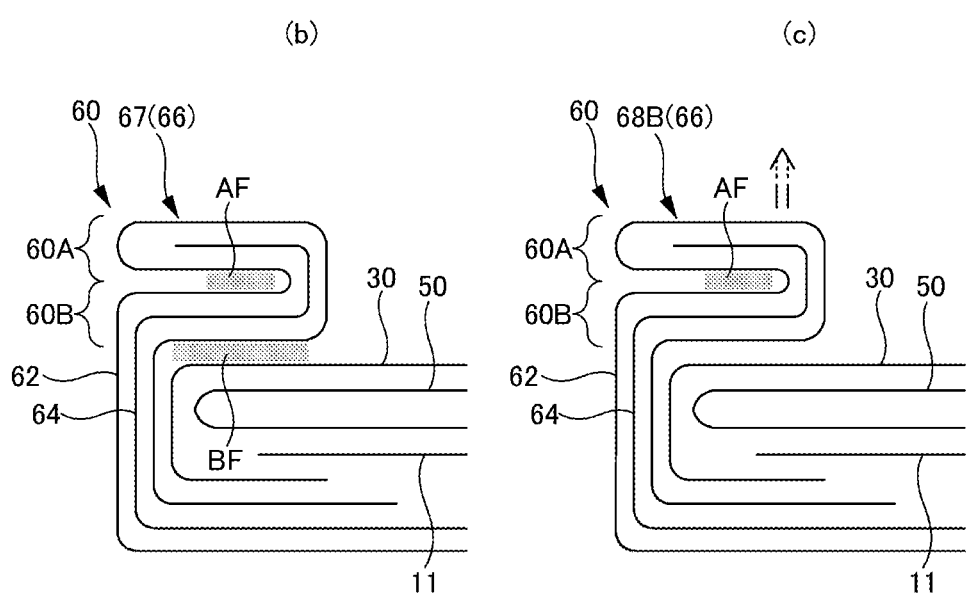

In addition, as illustrated in FIG. 11, when a back side half fallen part 68B in which the tip side part 60A is bonded to the root side part 60B in a fallen state continuously or adjacent to a front side of a back side fallen part 67, and the root side part 60B and the top sheet 30 are not bonded together is provided, only the root side part 60B is free, and the tip side part 60A is not fixed. Thus, the tip side part 60A of the three-dimensional gather rarely falls in an opposite direction due to an inclination toward an intergluteal cleft, which is preferable. (Since the back side half fallen part 68B comes into contact with a bulging portion of a buttock, even when the tip side part 60A is fixed, there is no concern that a gap may be generated between a body and the part). In addition, in this case, it is more preferable that the back side half fallen part 68B is the same as a front edge of the back side outer member 12B or extends to the center side in the front-back direction therefrom (that is, the back side half fallen part 68B includes an intersection position of the back side outer member 12B and the inner member 200). Further, in this case, it is preferable that a length of the back side half fallen part 68B in the front-back direction is longer than a length of the back side fallen part 67 in the front-back direction. In a normal case, it is preferable that a length of the back side fallen part 67 in the front-back direction is about 0.15 to 0.30 times a length of the inner member 200 in the front-back direction, and a dimension obtained by adding a length of the back side half fallen part 68B in the front-back direction thereto is about 0.20 to 0.35 times the length of the inner member 200 in the front-back direction. In FIG. 11, reference symbol AF denotes the hot melt adhesive that bonds the tip side part 60A and the root side part 60B, and reference symbol BF denotes the hot melt adhesive that bonds the root side part 60B and the top sheet 30.

As the gather nonwoven fabric 62, it is possible to use preferably a material obtained by performing a water repellent treatment on a nonwoven fabric which is flexible and excellent in uniformity/concealing property such as spun bond nonwoven fabric (SS, SSS, etc.), SMS nonwoven fabric (SMS, SSMMS, etc.), melt blown nonwoven fabric, etc. using silicone, etc. as necessary, and a fiber basis weight is preferably set to about 10 to 30 g/m$^2$. Rubber thread, etc. may be used as the gather elastic members 63. In the case of using spandex rubber thread, a fineness is preferably 470 to 1,240 dtex, more preferably 620 to 940 dtex. A stretch rate at the time of fixing is preferably 150 to 350%, more preferably 200 to 300%. It should be noted that the term "stretch rate" means a value when a natural length is taken as 100%. In addition, as illustrated in the figure, a waterproof film 64 may be interposed between two parts obtained by folding the gather nonwoven fabric 62. In this case, the gather nonwoven fabric 62 may be partially omitted in a portion in which the waterproof film 64 is present. However, to make appearance and texture of a product like cloth, it is necessary that an external surface at least from the base to the tip of the side gather 60 is formed by the gather nonwoven fabric 62 as in the illustrated embodiment.

The number of gather elastic members 63 provided in the free part of the side gather 60 is preferably 2 to 6, more preferably 3 to 5. An appropriate arrangement interval 60$d$ is 3 to 10 mm. When such a configuration is adopted, surface contact with a skin is easy in a range in which the gather elastic members 63 are disposed. The gather elastic members 63 may be disposed not only on the tip side but also on the root side.

In the free part 68 of the side gather 60, it is possible to use at least one of the hot melt adhesive based on various coating methods and fixing means based on material welding such as heat sealing, ultrasonic sealing, etc., for bonding of an internal layer and an external layer of the gather nonwoven fabric 62 and fixing of the gather elastic member 63 interposed therebetween. When the entire surfaces of the internal layer and the external layer of the gather nonwoven fabric 62 are bonded, flexibility is impaired. Thus, it is preferable that a portion other than a bonded portion of the gather elastic member 63 is not bonded or is weakly bonded. In the illustrated embodiment, the hot melt adhesive is applied only to the outer circumferential surface of the gather elastic member 63 by coating means such as a comb gun or a sure-wrap nozzle and interposed between the internal layer and the external layer of the gather nonwoven fabric 62, thereby performing fixing of the elongated elastic member to the internal layer and the external layer of the gather nonwoven fabric 62 and fixing of the gather nonwoven fabric 62 between the internal layer and the external layer only by the hot melt adhesive applied to the outer circumferential surface of the gather elastic member 63.

Similarly, for fixing of the waterproof film 64 and the gather nonwoven fabric 62 incorporated in the side gather 60 and fixing of the fallen part 67, it is possible to use at least one of a hot melt adhesive based on various coating methods and means based on material welding such as heat sealing, ultrasonic sealing, etc.

A dimension of the side gather 60 of the first embodiment may be appropriately determined. However, in the case of an infant disposable diaper, for example, as illustrated in FIG. 3, it is preferable that a standing height of the side gather 60 (a length of the main unit portion 66 in the width direction in the spread state) W2 is 15 to 60 mm, and particularly 20 to 40 mm. In addition, in a state in which the side gather 60 is folded flat to be parallel to the surface of the top sheet 30, it is preferable that a distance W1 between innermost folds is 60 to 190 mm, and particularly 70 to 140 mm.

Figure 12:
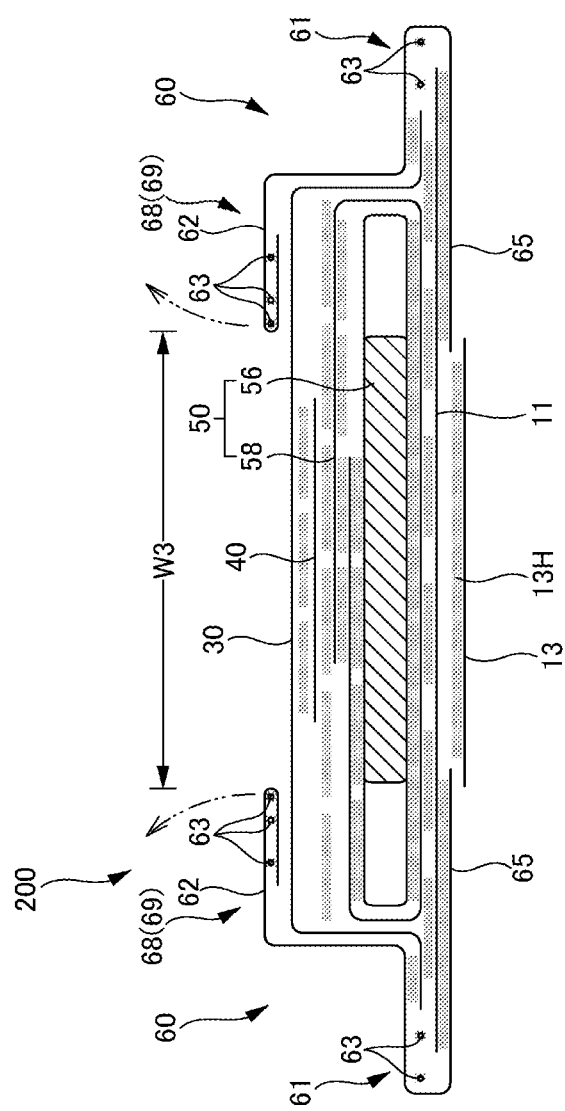
FIG. 12 is a cross-sectional view taken along 2-2 line of FIG. 1 illustrating another embodiment.
Figure 13:
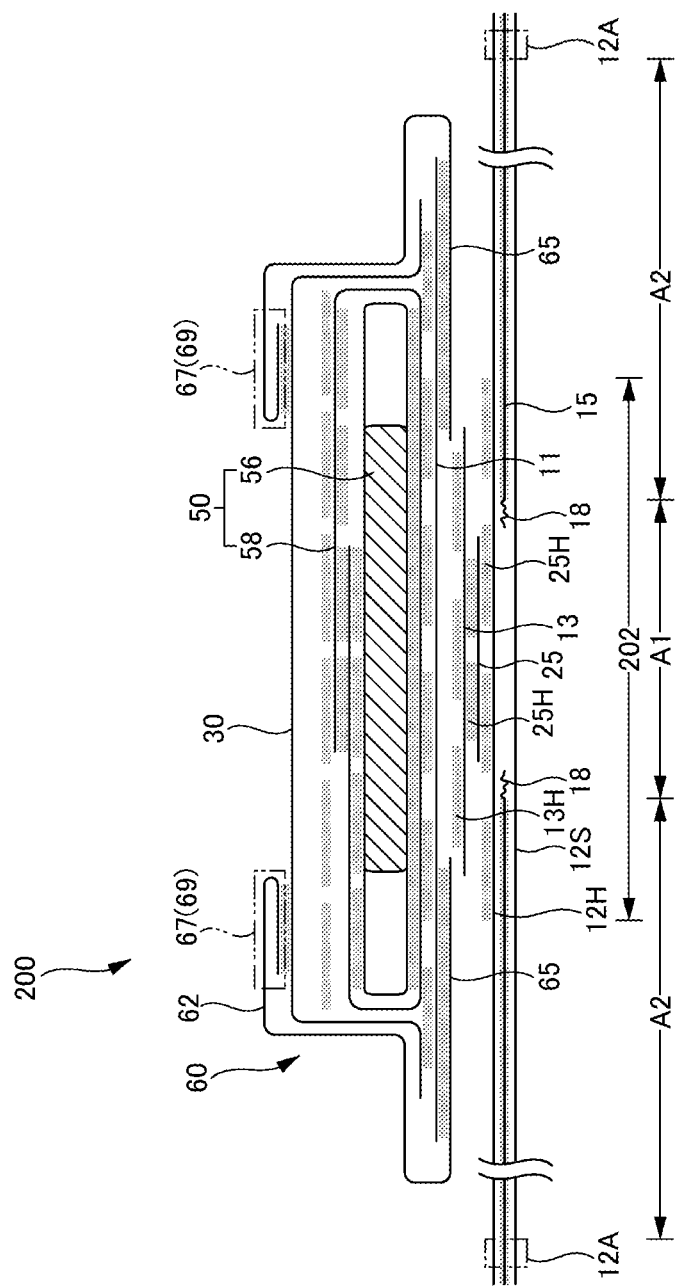
FIG. 13 is a cross-sectional view taken along 3-3 line of FIG. 1 illustrating another embodiment.

The side gather 60 of the first embodiment includes only the three-dimensional gather. However, the side gather 60 may include both the three-dimensional gather and the planar gather or include only the planar gather. FIG. 12 and FIG. 13 illustrate the side gather 60 of the second embodiment including both the three-dimensional gather and the planar gather. Each side gather 60 includes a first portion 61 (planar gather portion) protruding to a side of the inner member 200 from the root portion 65 fixed to a side portion on the back surface side of the liquid impervious sheet 11 in the inner member 200, and a second portion 69 (three-dimensional gather portion) protruding to the front surface side of the inner member 200 from the root portion 65 fixed to the both side portions of the top sheet 30 in the inner member 200. More specifically, the belt-shaped gather nonwoven fabric 62 having a length equal to the length of the inner member 200 in the front-back direction extends to a side from the root portion 65 and is folded back to the front surface side at a tip of the first portion 61, and a portion folded back to the front surface side reaches the second portion 69 through the first portion 61 and is folded back at a tip of the second portion 69. In a folded portion in the gather nonwoven fabric 62, facing portions are bonded by the hot melt adhesive, etc. In addition, both end portions of the second portion 69 in the front-back direction are set as the fallen parts 67 fixed to the side surface of the top sheet 30 in the fallen state, and an intermediate portion in the front-back direction positioned therebetween is set as the free part 68 which is not fixed. In at least the intermediate portion of the first portion 61 in the front-back direction and the free part 68 of the second portion 69, one gather elastic member 63 or a plurality of gather elastic members 63 with intervals in the width direction WD extending along the front-back direction LD is fixed in a stretched state, the free part 68 of the second portion 69 contracts in the front-back direction LD by a contraction force thereof to become a three-dimensional gather coming into contact with the periphery of the leg, and the first portion 61 contracts in the front-back direction LD to become a planar gather coming into contact with the periphery of the leg.

The three-dimensional gather in the side gather 60 of the second embodiment has a mode of standing to the center side in the width direction as a whole. However, the invention is not limited thereto, and it is possible to make an appropriate change by adopting the bending mode as in the side gather 60 of the first embodiment. Other points related to the second embodiment, for example, the material of the gather nonwoven fabric 62, the material of the gather elastic member 63, etc. are the same as those in the first embodiment, and a description thereof will be omitted.

(Absorbent Element)

The absorbent element 50 includes the absorbent body 56 and the package sheet 58 wrapping the entire absorbent body 56. The package sheet 58 may be omitted.

(Absorbent Body)

The absorbent body 56 can be formed by an assembly of fibers. As this fiber assembly, it is possible to use one obtained by accumulating short fibers of fluff pulp, synthetic fibers, etc., and a filament assembly obtained by opening a tow (fiber bundle) of synthetic fibers such as cellulose acetate as necessary. A fiber basis weight may be set to, for example, about 100 to 300 g/m$^2$ in the case of accumulating fluff pulp or short fibers, and may be set to, for example, about 30 to 120 g/m$^2$ in the case of the filament assembly. In the case of a synthetic fiber, the fineness is, for example, 1 to 16 dtex, preferably 1 to 10 dtex, more preferably 1 to 5 dtex. In the case of the filament assembly, the filaments may be non-crimped fibers, and are preferably crimped fibers. A degree of crimp of the crimped fibers can be set to, for example, about 5 to 75, preferably about 10 to 50, and more preferably about 15 to 50 per 2.54 cm. In addition, crimped fibers which are uniformly crimped are used in many cases. It is preferable to disperse and retain super absorbent polymer particles in the absorbent body 56.

Figure 7:
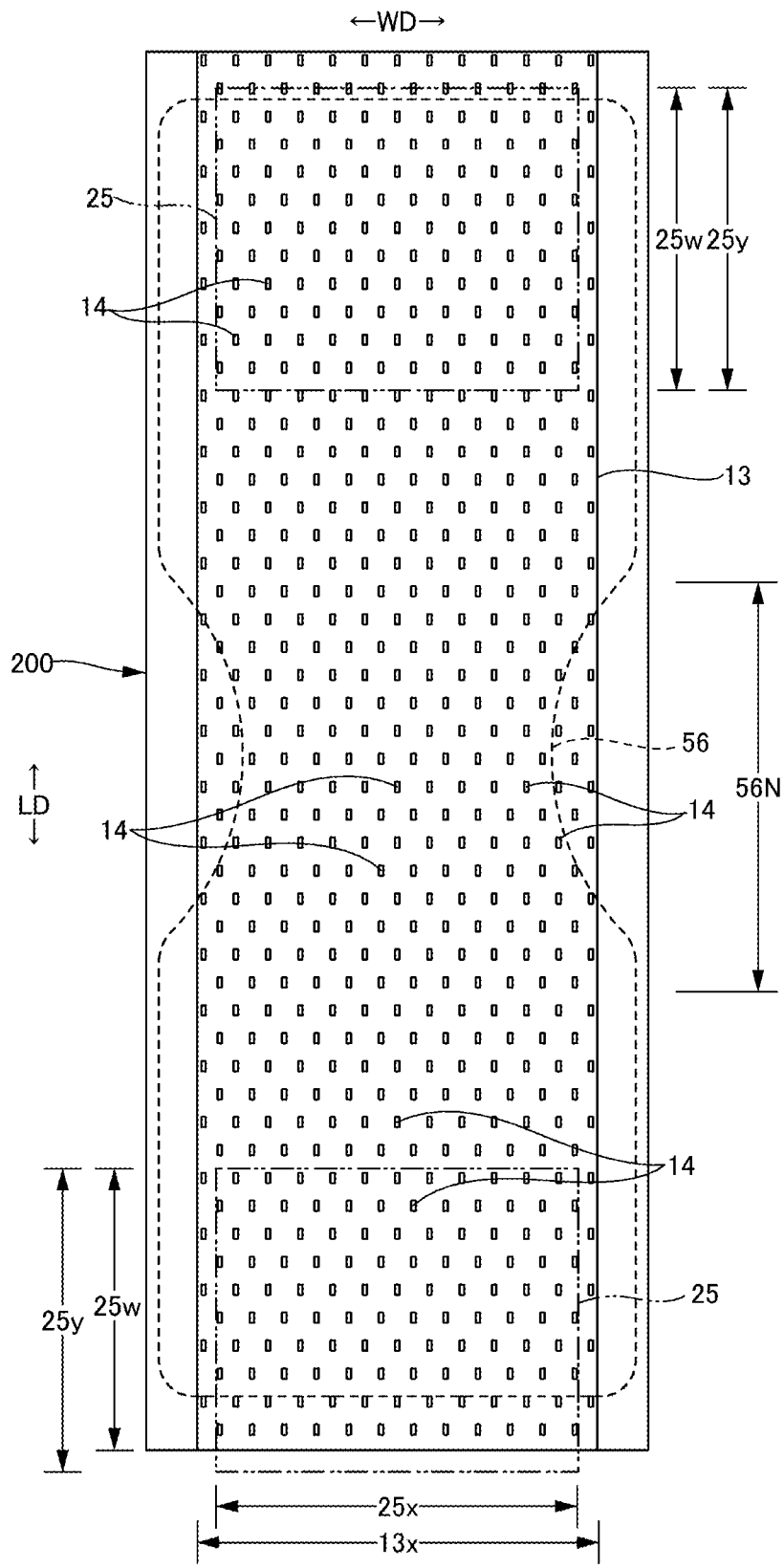
FIG. 7 is a plan view illustrating an external surface of an inner member in the spread state.

The absorbent body 56 may have a rectangular shape. However, when it has an hourglass shape having a narrower portion 56N whose width is narrower than that of both front and back sides in the middle in the front-back direction as illustrated in FIG. 1, FIG. 7, etc., fitting of the legs of the absorbent body 56 and the side gathers 60 to the peripheries is improved, which is preferable.

In addition, a dimension of the absorbent body 56 may be appropriately determined as long as the absorbent body 56 extends over a front, a back, a left, and a right of a ureteral outlet position. However, it is preferable that the absorbent body 56 extends to a peripheral edge portion of the inner member 200 or a vicinity thereof in the front-back direction LD and the width direction WD. Reference numeral 56X denotes a maximum width of the absorbent body 56.9

(Super Absorbent Polymer Particle)

A super absorbent polymer particle may be contained in a part or a whole of the absorbent body 56. The super absorbent polymer particle includes "powder" in addition to a "particle". A particle used in this type of disposable diapers may be used as the super absorbent polymer particle 54 without change. For example, it is desirable that the proportion of particles remaining on the sieve is 30 wt % or less by sieving (shaking for 5 minutes) using a 500 μm standard sieve (JIS Z 8801-1: 2006), and it is desirable that the proportion of particles remaining on the sieve is 60 wt % or more by sieving (shaking for 5 minutes) using a 180 μm standard sieve (JIS Z 8801-1: 2006).

A material of the super absorbent polymer particle may be used without particular limitation. However, a material having a water absorption capacity of 40 g/g or more is suitable. Examples of the super absorbent polymer particle include starch-based, cellulose-based and synthetic polymer-based ones, and it is possible to use a starch-acrylic acid (salt) graft copolymer, a saponified starch-acrylonitrile copolymer, crosslinked sodium carboxymethylcellulose, an acrylic acid (salt) polymer, etc. A normally used granular shape is suitable for a shape of the super absorbent polymer particle. However, another shape may be used.

A particle having a water absorption rate of 70 seconds or less, particularly 40 seconds or less is suitably used as the super absorbent polymer particle. When the water absorption rate is excessively low, so-called back-flow, in which a liquid supplied into the absorbent body 56 returns to the outside of the absorbent body 56, is likely to occur.

In addition, as the super absorbent polymer particle, one having a gel strength of 1000 Pa or more is preferably used. In this way, even when the absorbent body 56 is bulky, a sticky feeling after liquid absorption can be effectively suppressed.

A basis weight amount of the super absorbent polymer particle may be appropriately determined according to the absorption amount required for the use of the absorbent body 56. Therefore, even though it cannot be said unconditionally, the basis weight amount may be set to 50 to 350 g/m$^2$. When the basis weight amount of the polymer is less than 50 g/m$^2$, it is difficult to ensure the absorption amount. When the basis weight amount exceeds 350 g/m$^2$, the effect is saturated.

As necessary, a distribution density or a distribution amount of the super absorbent polymer particle may be adjusted in the plane direction of the absorbent body 56. For example, the distribution amount may be increased in a liquid excretion site than in other sites. In the case of considering a difference between men and women, it is possible to raise the distribution density (amount) on the front side for men and to raise the distribution density (amount) in the central part for women. Further, it is possible to provide a portion in which no polymer is present locally (for example, in a spot shape) in the planar direction of the absorbent body 56.

(Package Sheet)

When the package sheet 58 is used, it is possible to use tissue paper, particularly crepe paper, nonwoven fabric, poly-laminate nonwoven fabric, a sheet having an open small hole, etc. as a material thereof. However, it is desirable that the sheet is a sheet from which the super absorbent polymer particle does not come off. When a nonwoven fabric is used in place of crepe paper, a hydrophilic SMS nonwoven fabric (SMS, SSMMS, etc.) is particularly suitable, and polypropylene, polyethylene/polypropylene composite material, etc. may be used as the material. It is desirable that a basis weight is 5 to 40 g/m², particularly 10 to 30 g/m².

A package mode of the package sheet 58 may be appropriately determined. However, from viewpoints of ease of manufacturing, prevention of leakage of the super absorbent polymer particle from front and back end edges, etc., in a preferable mode, winding is performed in a cylindrical shape to surround the front and back surfaces and both side surfaces of the absorbent body 56, front and back edge portions thereof are allowed to protrude from the front and the back of the absorbent body 56, and an overlapping portion of a winding portion and front and back protruding portions are bonded by bonding means such as a hot melt adhesive, material welding, etc.

(Outer Member)

Figure 23:
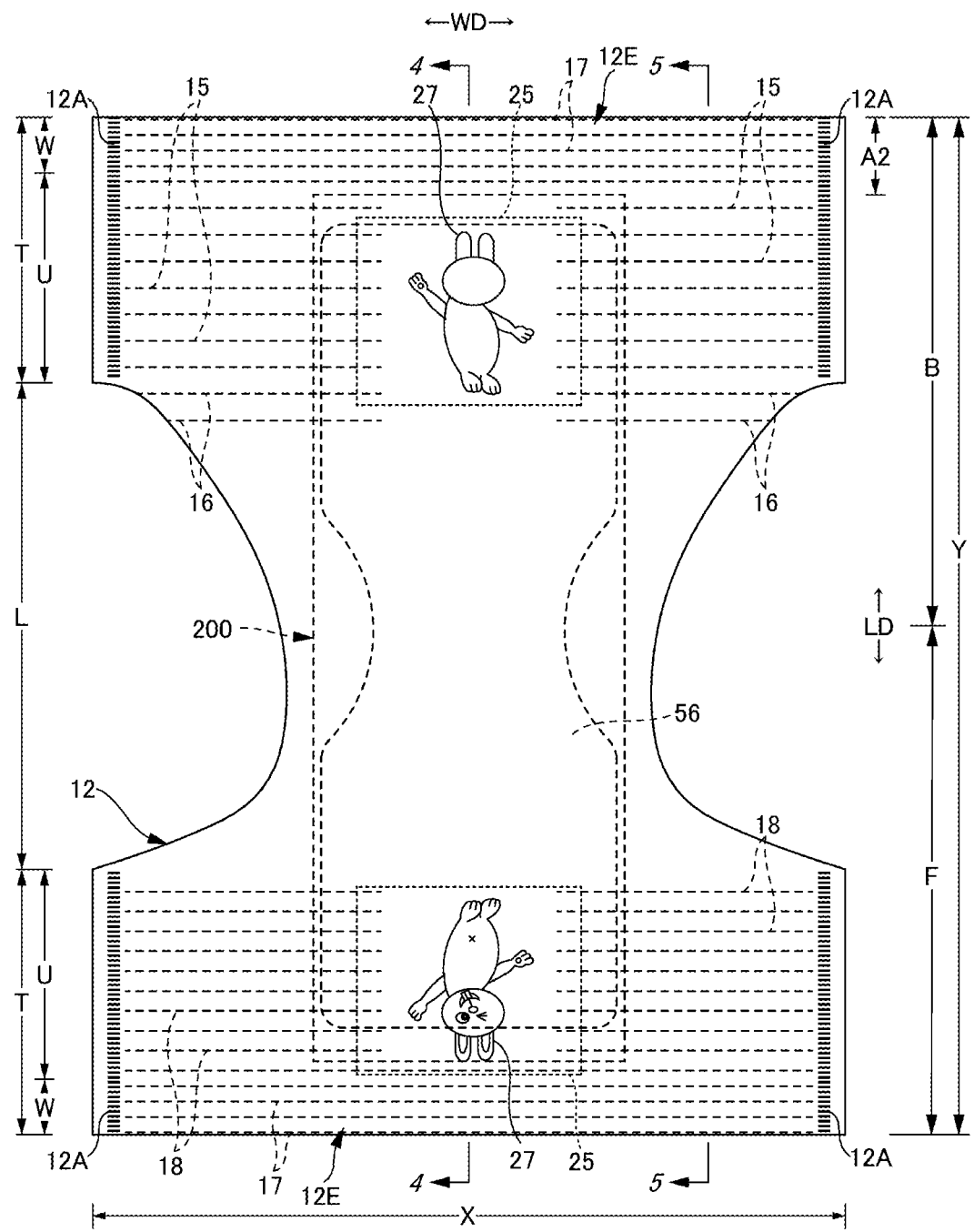
FIG. 23 is a plan view illustrating an external surface of the underpants-type disposable diaper in the spread state.
Figure 24:
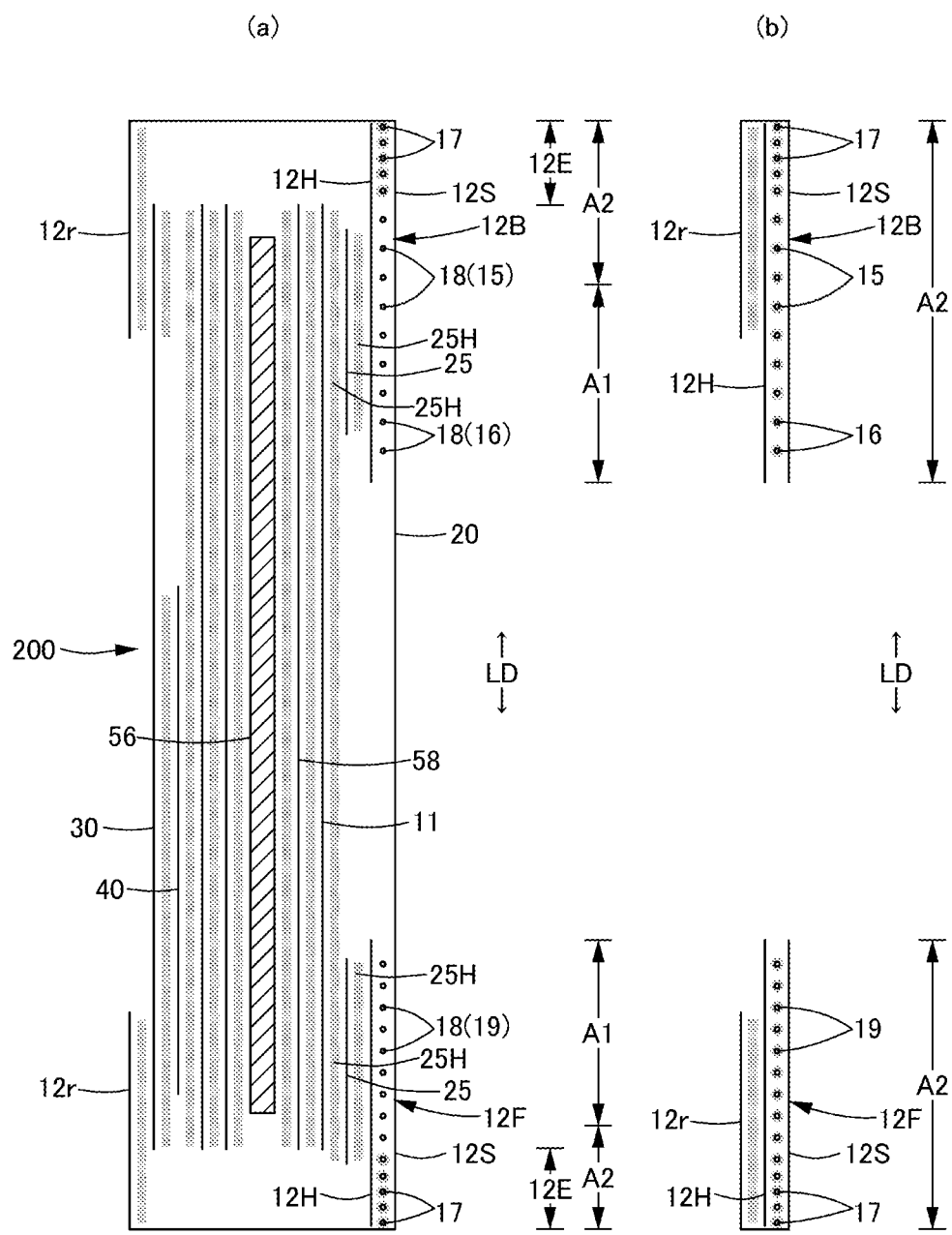
FIG. 24(a) is a cross-sectional view taken along 4-4 line of FIG. 23.
FIG. 24(b) is a cross-sectional view taken along 5-5 line of FIG. 23.

The outer members 12F and 12B do not correspond to an integral outer member 12 that continues through the crotch from the front body F to the back body B illustrated in FIG. 23 and FIG. 24, and includes the front side outer member 12F corresponding to a portion forming at least the lower torso portion of the front body F and the back side outer member 12B corresponding to a portion forming at least the lower torso portion of the back body B. The front side outer member 12F and the back side outer member 12B are not continuous on the crotch side and are spaced apart in the front-back direction LD. For example, a spaced distance 12d may be set to about 150 to 250 mm.

The outer members 12F and 12B have lower torso portions which are front-back direction zones corresponding to the lower torsos T. In addition, in this embodiment, the back side outer member 12B has a longer front-back direction dimension than that of the front side outer member 12F, the front side outer member 12F does not have a portion corresponding to the intermediate region L, and the back side outer member 12B has a gluteal cover portion C extending from the lower torsos T to the intermediate region L side. Although not illustrated, it is possible to adopt an embodiment in which an inguinal cover portion extending from the lower torso T to the intermediate region L side is provided in the front side outer member 12F, an inguinal cover portion is provided and the gluteal cover portion is not provided, or a part corresponding to the intermediate region L is not provided in both the front side outer member 12F and the back side outer member 12B. In addition, in the illustrated embodiment, a lower edge of the gluteal cover portion C is formed in a linear shape along the width direction WD similarly to the lower edge of the front side outer member 12F. However, the lower edge may be formed in a curved shape located on the waist opening side toward an outer side in the width direction.

A front-back direction dimension of a side edge of the gluteal cover portion C may be determined as appropriate. However, when the dimension is excessively long, a corner on the leg opening LO side of the side edge may flicker and the appearance and wearing feeling may deteriorate, and thus the dimension is preferably 20 mm or less.

As illustrated in FIG. 4 and FIG. 5, the outer members 12F and 12B are obtained by bonding an outer sheet layer 12S and an inner sheet layer 12H located on an outside and an inside of elastic members 15 to 19 described below using bonding means such as the hot melt adhesive or welding. A sheet material forming the outer sheet layer 12S and a sheet material forming the inner sheet layer 12H may be formed of one common sheet material or separate sheet materials. That is, in the former case, the inner sheet layer 12H and the outer sheet layer 12S are formed by an inner portion and an outer portion of one sheet material, respectively, which is folded back at an edge of the waist opening WO (which may be a crotch side edge) in a part or a whole of the outer member. The former embodiment is advantageous in that the number of materials of the sheet material is small, and the latter is advantageous in that positional shift rarely occurs when the inner sheet layer 12H and the outer sheet layer 12S are bonded. The illustrated corresponds to the latter case, and the sheet material forming the inner sheet layer 12H extends only to the edge of the waist opening WO. However, the sheet material forming the outer sheet layer 12S wraps around the waist side edge of the sheet material of the inner sheet layer 12H and is folded back inside the sheet material, and this folded portion 12r extends to cover up to a waist side end portion of the inner member 200.

As the sheet material used for the outer sheet layer 12S and the inner sheet layer 12H, any material may be used without particular restriction. However, a nonwoven fabric is preferably used. Examples thereof may include a synthetic fiber such as polyolefin synthetic fiber such as polyethylene, polypropylene, etc., a polyester synthetic fiber, a polyamide synthetic fiber, etc., or a nonwoven fabric containing a mixed fiber, a composite fiber, etc. using two types or more thereof. Further, the nonwoven fabric may be manufactured by any process. Examples of a processing method may include a known method such as a spun lace method, a spun bond method, a thermal bond method, a melt blown method, a needle-punch method, an air-through method, a point bond method, etc. When the nonwoven fabric is used, a basis weight thereof is preferably set to about 10 to 30 g/m².

In addition, a total basis weight of the outer members 12F and 12B is preferably about 20 to 60 g/m².

(Stretchable Region/Non-Stretchable Region)

In the outer members 12F and 12B, to enhance fitting to the periphery of the truck of the wearer, the elastic members 15 to 19 are provided between the outer sheet layer 12S and the inner sheet layer 12H, and a stretchable region A2 that elastically stretches and contracts in the width direction WD in response to stretch and contraction of the elastic member is formed. In this stretchable region A2, in a natural length state, the outer sheet layer 12S and the inner sheet layer 12H contract in response to contraction of the elastic member, and wrinkles and pleats are formed. Stretch in a longitudinal direction of the elastic member allows stretch up to a predetermined stretch rate at which the outer sheet layer 12S and the inner sheet layer 12H fully extend without wrinkles. As the elastic members 15 to 19, in addition to an elongated elastic member (not illustrated example) such as rubber thread, it is possible to use a known elastic member such as a belt-shaped, net-shaped, or film-shaped elastic member without particular limitation. Synthetic rubber or natural rubber may be used as the elastic members 15 to 19.

For bonding of the outer sheet layer 12S and the inner sheet layer 12H in the outer members 12F and 12B and fixing of the elastic members 15 to 19 interposed therebetween, it is possible to use at least one of a hot melt adhesive based on various coating methods and fixing means based on material welding such as heat sealing, ultrasonic sealing, etc. Since flexibility deteriorates when the entire surfaces of the outer members 12F and 12B are firmly fixed, it is preferable that a portion other than bonded portions of the elastic members 15 to 19 is not bonded or is weakly bonded. In the illustrated, the hot melt adhesive is applied only to outer circumferential surfaces of the elastic members 15 to 19 by coating means such as a comb gun or a sure-wrap nozzle and the elastic members 15 to 19 are interposed between both the sheet layers 12S and 12H, thereby performing fixing of the elastic members 15 to 19 to both the sheet layers 12S and 12H and fixing between both the sheet layers 12S and 12H only by the hot melt adhesive applied to the outer circumferential surfaces of the elastic members 15 to 19. The elastic members 15 to 19 can be fixed to the outer sheet layer 12S and the inner sheet layer 12H only at both end portions in an extending direction in the stretchable region.

The elastic members 15 to 19 of the illustrated embodiment will be described in more detail. Between the outer sheet layer 12S and the inner sheet layer 12H in the waist portion W of the outer members 12F and 12B, a plurality of waist portion elastic members 17 are attached at intervals in the front-back direction to be continuous over a whole in the width direction WD. In addition, one or a plurality of waist portion elastic members among the waist portion elastic members 17 arranged in a region adjacent to the lower waist portion U may overlap the inner member 200 or may be provided on both sides of a width direction center portion overlapping the inner member 200 in the width direction except for the width direction center portion. As the waist portion elastic members 17, it is preferable to provide about three to twenty two rubber threads having a fineness of about 155 to 1,880 dtex, particularly 470 to 1,240 dtex (in the case of synthetic rubber. In the case of natural rubber, a cross-sectional area is about 0.05 to 1.5 mm$^2$, particularly 0.1 to 1.0 mm$^2$) at an interval of 4 to 12 mm, and it is preferable that a stretch rate of the waist portion W in the width direction WD resulting therefrom is about 150 to 400%, particularly 220 to 320%. In addition, it is unnecessary to use the waist portion elastic members 17 having the same fineness or set the same stretch rate in the whole waist portion W in the front-back direction LD. For example, the fineness or the stretch rate of the waist portion elastic members 17 may be different between an upper part and a lower part of the waist portion W.

In addition, a plurality of lower waist portion elastic members 15 and 19 formed of an elongated elastic member is attached at an interval in the front-back direction between the outer sheet layer 12S and the inner sheet layer 12H in the lower waist portion U of the outer members 12F and 12B.

As the lower waist portion elastic members 15 and 19, it is preferable to provide about five to thirty rubber threads having a fineness of about 155 to 1,880 dtex, particularly 470 to 1,240 dtex (in the case of synthetic rubber. In the case of natural rubber, a cross-sectional area is about 0.05 to 1.5 mm$^2$, particularly 0.1 to 1.0 mm$^2$) at an interval of 1 to 15 mm, particularly 3 to 8 mm, and it is preferable that a stretch rate of the lower waist portion U in the width direction WD resulting therefrom is about 200 to 350%, particularly 240 to 300%.

In addition, a cover portion elastic member 16 formed of an elongated elastic member is attached between the outer sheet layer 12S and the inner sheet layer 12H in the gluteal cover portion C of the back side outer member 12B.

As the cover portion elastic member 16, it is preferable to provide one or a plurality of rubber threads having a fineness of about 155 to 1,880 dtex, particularly 470 to 1,240 dtex (in the case of synthetic rubber. In the case of natural rubber, a cross-sectional area is about 0.05 to 1.5 mm$^2$, particularly 0.1 to 1.0 mm$^2$) with intervals in the front-back direction, and it is preferable that a stretch rate of the gluteal cover portion C in the width direction WD resulting therefrom is about 150 to 300%, particularly 180 to 260%.

In the case of providing the cover portion elastic member 16, it is preferable that a front-back direction interval between the cover portion elastic member 16 located closest to the leg opening LO side at a side edge Cs of the gluteal cover portion C and a leg opening side edge Ce of the gluteal cover portion C is 0.9 to 1.1 times a width direction dimension W3 from a side edge of the back side outer member 12B to a side edge of the side seal portions 12A on a center side in the width direction, because a corner of the side edge Cs of the gluteal cover portion C on a side of the leg openings LO is almost inconspicuous. In particular, in this case, it is preferable to provide one cover portion elastic member 16 or two cover portion elastic members 16 at an interval of 5 mm or less in the front-back direction LD. In addition, it is preferable that a front-back direction interval from the cover portion elastic member 16 located closest to the waist side to the lower waist portion elastic member 15 adjacent to the waist side is 15 mm or more and widest among intervals of all elastic members in the back side outer member 12B, because a portion on the waist side of the cover portion elastic member 16 appears to be wider than a portion on the leg opening side of the cover portion elastic member 16 in the back side outer member 12B, so that protrusion of the corner on the leg opening LO side of the side edge Cs of the gluteal cover portion C becomes less conspicuous.

Figure 22:
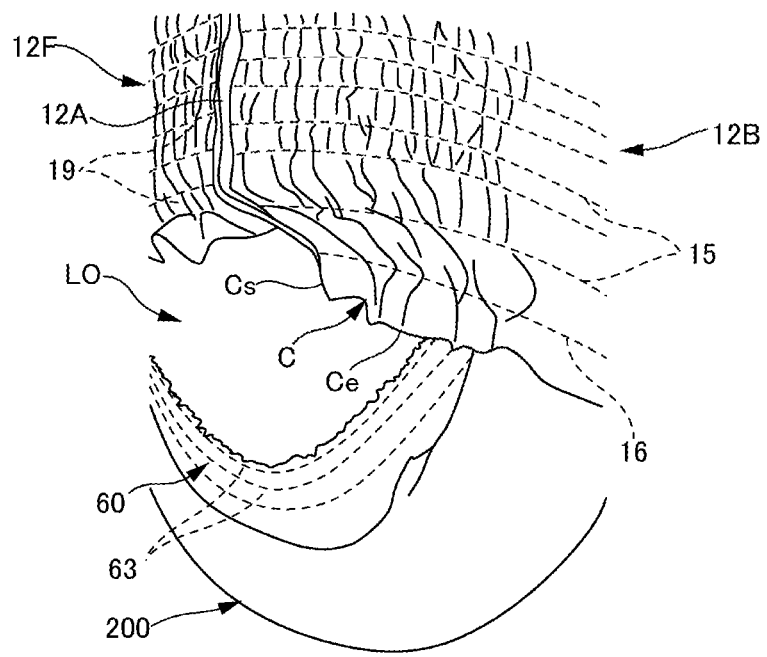
FIG. 22 is a perspective view illustrating a main part of the underpants-type disposable diaper.
Figure 22:
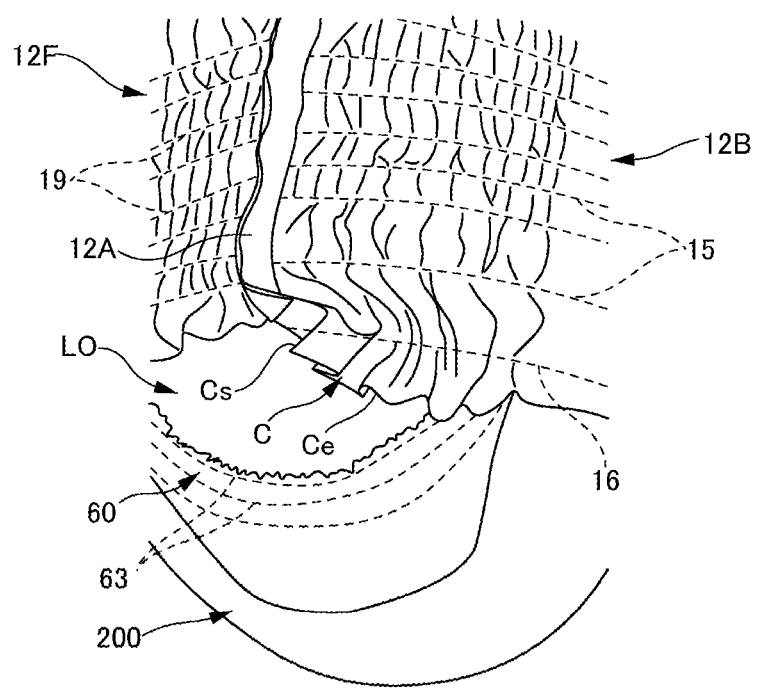

Here, if the cover portion elastic member 16 is disposed only on the leg opening LO side in the gluteal cover portion C, when the gluteal cover portion C contracts together with the cover portion elastic member 16 as illustrated in FIG. 22(a), the leg opening LO side of the gluteal cover portion C is drawn to the center side in the width direction WD. Thus, even when the edge Ce of the gluteal cover portion C on the leg opening LO side is linear along the width direction WD, the edge Ce of the gluteal cover portion C on the leg opening LO side diagonally inclines downward toward the center side in the width direction WD, and fitting with respect to a gluteal fold is improved. In this instance, the side edge Cs of the gluteal cover portion C diagonally inclines downward toward the center side in the width direction WD so that the corner of the side edge Cs of the gluteal cover portion C on the leg opening LO side is inconspicuous and the appearance does not deteriorate.

Meanwhile, in a case in which the cover portion elastic member 16 is disposed only on the waist side in the gluteal cover portion C, when the gluteal cover portion C contracts together with the cover portion elastic member 16 as illustrated in FIG. 22(b), the waist side of the gluteal cover portion C is drawn to the center side in the width direction.

Thus, even when the edge Ce of the gluteal cover portion C on the leg opening LO side is linear along the width direction WD, the side edge Cs of the gluteal cover portion C warps backward to a side, the edge Ce of the gluteal cover portion C on the leg opening LO side diagonally inclines downward toward the center side in the width direction, and fitting with respect to the gluteal fold is improved. In this instance, even though the side edge Cs of the gluteal cover portion C warps backward to the side, the corner of the side edge Cs of the gluteal cover portion C on the leg opening LO side does not greatly protrude to the side of the side seal portions 12A. Thus, the corner of the side edge Cs of the gluteal cover portion C on the leg opening LO side is inconspicuous, and the appearance does not deteriorate.

In addition, in a case in which a front-back direction dimension at the side edge Cs of the gluteal cover portion C is 0.9 to 1.1 times a width direction dimension W3 from the side edge of the back side outer member 12B to the side edge of the center side of the side seal portions 12A in the width direction WD, the cover portion elastic member 16 of the gluteal cover portion C may not be provided. In this case, even though the side edge Cs of the gluteal cover portion C easily warps backward to the side due to an influence of contraction of the lower waist portion by the lower waist portion elastic member 15, the corner of the side edge Cs of the gluteal cover portion C on the leg opening LO side rarely protrudes from the side edge of the diaper. Thus, this corner is inconspicuous, and the appearance does not deteriorate.

When the inguinal cover portion is provided in the front side outer member 12F, the cover portion elastic member may be similarly provided.

In a case in which the elastic members 15, 16, and 19 are provided in the front-back direction zones having the absorbent body 56 as in the lower waist portion U or the gluteal cover portion C of the illustrated embodiment, a middle portion in the width direction including a part or a whole of a portion overlapping the absorbent body 56 in the width direction WD (preferably including the entire inner and outer joined portions 201 and 202) is set as a non-stretchable region A1, and both sides thereof in the width direction are set as a stretchable region A2 to prevent contraction of the absorbent body 56 in the width direction WD in a part or a whole thereof. The waist portion W is preferably set as the stretchable region A2 over the whole in the width direction WD. However, similarly to the lower waist portion U, the non-stretchable region A1 may be provided in the middle in the width direction.

The stretchable region A2 and the non-stretchable region A1 can be constructed by supplying the elastic members 15 to 17 and 19 between the inner sheet layer 12H and the outer sheet layer 12S, fixing the elastic members 15, 16, and 19 at least at both end portions of the stretchable region A2 in the extending direction through the hot melt adhesive, not fixing the elastic members 15, 16, and 19 in a region corresponding to the non-stretchable region A1, and cutting the elastic members 15, 16, and 19 at one place in the middle in the width direction by pressing and heating or finely cutting almost all of the elastic members 15, 16, and 19 by pressing and heating in the region corresponding to the non-stretchable region A1, thereby killing elasticity in the non-stretchable region A1 while leaving elasticity in the stretchable region A2. In the former case, as illustrated in FIG. 4, in the non-stretchable region A1, a remaining cut portion continuing from the elastic members 15, 16, and 19 of the stretchable region A2 is left between the outer sheet layer 12S and the inner sheet layer 12H in a state of contracting to a natural length as an unnecessary elastic member 18 alone. In the latter case, although not illustrated, the remaining cut portion continuing from the elastic members 15, 16, and 19 of the stretchable region A2 and a cut piece of the elastic member not continuing from the elastic members 15, 16, and 19 of both the stretchable region A2 are left between the outer sheet layer 12S and the inner sheet layer 12H in a state of contracting to a natural length as an unnecessary elastic member alone.

(Display Sheet)

As illustrated in FIG. 2, FIG. 5, FIG. 7, and FIG. 8, a display sheet 25 having a display 27 of a character, etc. is interposed between at least one of the front side outer member 12F and the back side outer member 12B and the inner member 200, and a display of the display sheet 25 is seen through the outer members 12F and 12B. In the case of a mode in which the display sheet 25 is interposed between the outer members 12F and 12B and the inner member 200, a process of cutting the elastic members 15, 16, and 19 for forming the non-stretchable region A1 can be performed without the display sheet 25 at the time of manufacture. Thus, a trace of cutting is not left on the display sheet 25, and deterioration of the appearance can be prevented.

A resin film is used as a material of the display sheet 25 in terms of being suitable for high-definition printing. In the case of using a resin film having high opacity, a printed part needs to be provided on an external surface of the display sheet 25. However, for example, in the case of using a resin film having high transparency, a printed part may be provided on an internal surface of the display sheet 25.

The display 27 applied to the display sheet 25 is not particularly limited, and it is possible to apply a display such as a pattern (including a picture and a one-point character) for decoration, a function display such as a usage method, assistance for use, a size, etc., or a mark indication such as a manufacturer, a product name, a distinctive function, etc. by printing, etc.

At least one of the internal surface and the external surface of the display sheet 25 is bonded to a facing surface through a hot melt adhesive 25H.

A dimension of the display sheet 25 may be appropriately determined. However, in a normal case, it is preferable that the display sheet 25 is provided to be smaller than or equal to a width of the inner member 200 within a width direction range overlapping the inner member 200. Specifically, when the display sheet 25 is 50 to 100% of the width of the inner member 200, it is easy to stick to the inner member 200 side at the time of manufacture, which is preferable. In addition, it is preferable that a width 25x of the display sheet 25 is wider than a width 13x of the cover nonwoven fabric 13 described below.

The display sheet 25 may be disposed within a range overlapping the inner member 200 as the display sheet 25 disposed in the back body B illustrated in the figure. At least one display sheet 25 is made of a liquid impervious resin film. When the display sheet 25 extends from the region overlapping the inner member 200 to an inside of a waist extended section 12E extending to the waist opening WO side of the waist side edge of the inner member 200 as the display sheet 25 disposed in the front body F illustrated in the figure, it is possible to prevent seepage of urine and loose stools in the waist extended section 12E of the front side outer member 12F by blocking urine and loose stools leaking from the waist side end portion of the inner member 200 to the waist side using the display sheet 25. Unlike the illustrated embodiment, together with or in place of the display sheet 25 of the front body F, the display sheet 25 disposed in the back body B can be extended from the region overlapping the inner member 200 to an inside of the waist extended section 12E. As the liquid impervious resin film, it is possible to select the same material as that of the liquid impervious sheet 11. In particular, it is preferable to use a plastic film having moisture permeability similarly to the liquid impervious sheet 11.

Figure 21:
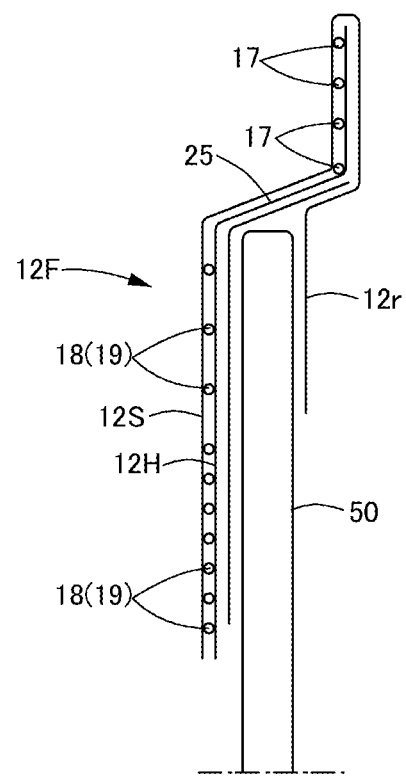
FIG. 21 is a cross-sectional view illustrating a main part of a portion having a display sheet.

When the display sheet 25 is extended to the inside of the waist extended section 12E, it is more preferable that an elastic member that contracts a width direction range corresponding to at least an intermediate part of the display sheet 25 in the width direction is provided at a position spaced 5 mm or more apart to the waist opening WO side from the waist side edge of the inner member 200 in the waist extended section 12E. In the illustrated embodiment, the waist portion elastic member 17 corresponds to the elastic member of this arrangement. While a region in which the outer members 12F and 12B overlap the inner member 200 has high rigidity and rarely bends, the waist extended section 12E has low rigidity and easily bends. Thus, as illustrated in FIG. 21, when the display sheet 25 contracts in the width direction toward the waist side by the waist portion elastic member 17, and a portion between the elastic member and the inner member 200 in the waist extended section 12E bends toward the skin side at a boundary with the inner member 200, a portion of the waist extended section 12E having the display sheet 25 rises, and a blocking wall for urine and loose stools is formed. Therefore, it is possible to improve prevention of seepage of urine and loose stools in the waist extended section 12E of the outer members 12F and 12B. In this case, it is preferable that the waist extended section 12E only includes a nonwoven fabric that forms the outer sheet layer 12S and the inner sheet layer 12H, because a difference in rigidity between the region in which the outer members 12F and 12B overlap the inner member 200 and the waist extended section 12E increases. In addition, as the number of overlapping sheets at a waist side edge portion of the inner member 200 increases, the difference in rigidity increases, which is preferable. Specifically, it is preferable to have three or more number difference. In particular, when at least the liquid impervious sheet 11 including the plastic film is present or the package sheet 58 including crepe paper is further present at the waist side edge portion of the inner member 200, rigidity increases, which is preferable. In addition, it is preferable that the bulky intermediate sheet 40 extends to the waist side edge portion of the inner member 200. It is preferable that the region in which the outer members 12F and 12B overlap the inner member 200 coincides with the non-stretchable region A1 so that the region does not bend.

A front-back direction length 25y of that portion of the display sheet 25 which is located in the waist extended section 12E is not particularly limited. However, in a normal case, the length is preferably 5 mm or more. In addition, when the display sheet 25 extends to at least an elastic member located closest to the inner member 200 side (in the illustrated embodiment, a member located closest to the crotch side among the waist portion elastic members 17), it is particularly preferable for improving prevention of seepage of urine and loose stools in the waist extended section 12E of the outer members 12F and 12B.

(Cover Nonwoven Fabric)

In the outer member separated type underpants-type disposable diaper, the inner member 200 is exposed between the front side outer member 12F and the back side outer member 12B, and thus the disposable diaper includes the cover nonwoven fabric 13 that covers the back surface of the inner member 200 from between the front side outer member 12F and the inner member 200 to between the back side outer member 12B and the inner member 200 so that the liquid impervious sheet 11 is not exposed to the back surface of the inner member 200.

Characteristically, the cover nonwoven fabric 13 is a perforated nonwoven fabric in which a large number of holes 14 penetrating the front and back are provided at intervals, and extends in the front-back direction LD to have a portion located between the display sheet 25 and the liquid impervious sheet 11. When the cover nonwoven fabric 13 extends to a space between the display sheet 25 and the liquid impervious sheet 11 as described above, ventilation is allowed through the nonwoven fabric with the holes 14 from the outside of the disposable diaper to the space between the display sheet 25 and the liquid impervious sheet 11, and thus it is possible to prevent deterioration of the air permeability when the resin film is used as the material of the display sheet 25.

Although not illustrated, at least, a perforated nonwoven fabric dedicated for improving air permeability may be provided separately from the cover nonwoven fabric 13. The perforated nonwoven fabric extends from a crotch side edge of the outer members 12F and 12B overlapping the display sheet 25 to a space between the display sheet 25 and the liquid impervious sheet 11 on the waist opening side. In addition, in the case of having the display sheet 25 on both the front and the back, the cover nonwoven fabric 13 may merely extend to a space between the display sheet 25 and the liquid impervious sheet 11 in only either one of the front side outer member 12F and the back side outer member 12B.

There are no particular restrictions on the type of fibers of the perforated nonwoven fabric and a processing method for bonding (entanglement) of the fibers, and the same materials as the materials for the outer members 12F and 12B can be appropriately selected. However, it is desirable to use an air-through nonwoven fabric. In this case, it is preferable that a basis weight is 20 to 40 g/m$^2$ and a thickness is 0.3 to 1.0 mm.

Figure 2:
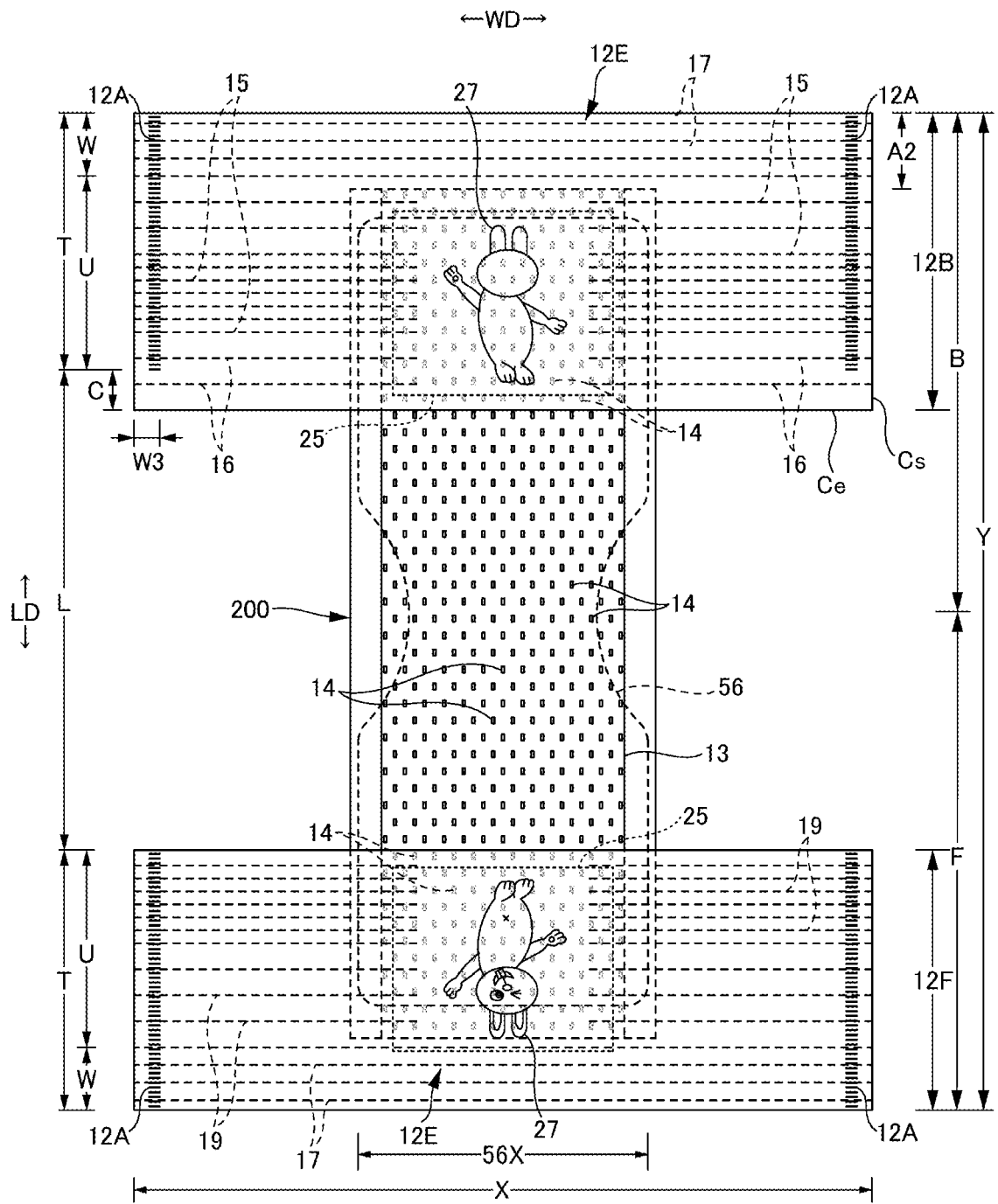
FIG. 2 is a plan view illustrating an external surface of the underpants-type disposable diaper in the spread state.
Figure 8:
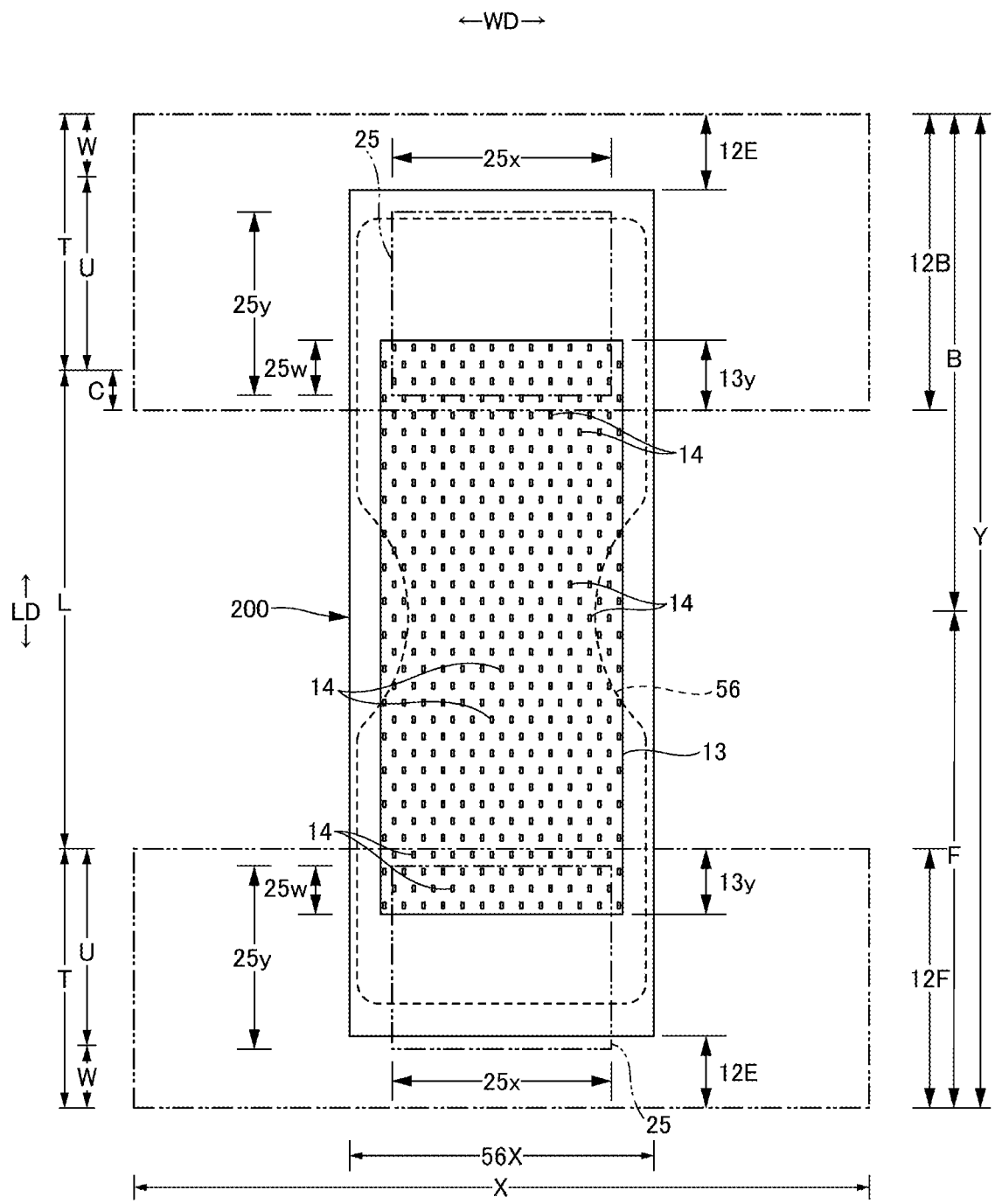
FIG. 8 is a plan view illustrating the external surface of the inner member in the spread state together with a contour of an outer member.

The front-back direction zones of the cover nonwoven fabric 13 are not particularly limited as long as the front-back direction zones have a portion located between the display sheet 25 and the liquid impervious sheet 11. The front-back direction zones may extend in the front-back direction LD over a whole area from a front end to a back end of the inner member 200 as illustrated in FIG. 2, FIG. 5, and FIG. 7, and may extend in the front-back direction LD from a middle position in the front-back direction in a region overlapping the front side outer member 12F and the inner member 200 to a middle position in the front-back direction in a region overlapping the back side outer member 12B and the inner member 200 as illustrated in FIG. 8. A front-back direction length 25w of an overlapping portion of the display sheet 25 and the cover nonwoven fabric 13 is preferably 25 to 100% of a front-back direction length 25y of the display sheet 25. In addition, in the case of an embodiment illustrated in FIG. 8, a front-back direction length 13y of an overlapping portion of the cover nonwoven fabric 13 and the front side outer member 12F and a front-back direction length 13y of an overlapping portion of the cover nonwoven fabric 13 and the back side outer member 12B may be determined as appropriate. However, in a normal case, each of the lengths may be set to about 20 to 40 mm.

A width direction range of the cover nonwoven fabric 13 is set to a range in which an exposed portion of the back surface of the liquid impervious sheet 11 can be concealed. For this reason, in the illustrated embodiment, the liquid impervious sheet 11 is exposed between bases of the left and right side gathers 60, and thus the cover nonwoven fabric 13 is provided to cover at least a width direction range from the back surface side of the base portion of one of the side gathers 60 to the back surface side of the base portion of the other one of the side gathers 60. In this way, the liquid impervious sheet 11 can be concealed by the cover nonwoven fabric 13 and the gather nonwoven fabric 62 of the side gather 60, and the holes 14 in both end portions of the cover nonwoven fabric 13 in the width direction are not concealed by the gather nonwoven fabric 62 when viewed from the external surface. In addition, when the side edge of the cover nonwoven fabric 13 is the same as a side edge of a portion of the absorbent body 56 having a narrowest width (a maximum width in the case of not having the narrower portion 56N. a portion having a narrowest width in the narrower portion 56N in the case of having the narrower portion 56N) or is located on a center side thereof in the width direction, the cover nonwoven fabric 13 is located only in a portion in which the entire cover nonwoven fabric 13 overlaps the absorbent body 56, that is, a portion in which rigidity is high and wrinkles and folds are rarely generated. Thus, both side portions of the cover nonwoven fabric 13 rarely contracts in the front-back direction LD. Further, wrinkles are rarely formed and crushing of the holes 14 rarely occurs in both side portions of the cover nonwoven fabric 13. In addition, even when the both end portions of the cover nonwoven fabric 13 in the width direction do not cover the back surface side of the base portion of the side gather 60, and the gather nonwoven fabric 62 covers the back surface side of the both end portions of the cover nonwoven fabric 13 in the width direction, the liquid impervious sheet 11 can be concealed by the cover nonwoven fabric 13 and the gather nonwoven fabric 62. In this case, the both end portions of the cover nonwoven fabric 13 are covered with the gather nonwoven fabric 62, and thus there is an advantage that the both side portions of the cover nonwoven fabric 13 are hardly peeled off from the liquid impervious sheet 11.

As long as the holes 14 are formed in at least a portion overlapping the display sheet 25 in the front-back direction, the cover nonwoven fabric 13 may have a region not including the holes 14 in a part in the front-back direction LD. However, it is desirable to provide the holes 14 in the whole area in the front-back direction in consideration of the effect of improving the air permeability. Meanwhile, in a mode in which a region not having the holes 14 is included in the both end portions of the cover nonwoven fabric 13 in the width direction WD, when the holes 14 are formed by a method other than punching using a cutter, a fiber of a peripheral portion 14e of the hole 14 is retracted to the outside or in a vertical direction as described below to warp the peripheral portion 14e of the hole 14, and a perforated region becomes thicker than a nonporous region. Thus, when the material of the cover nonwoven fabric 13 is stored in a rolled state, a part of the nonporous region is loosely wound, and there is concern that wrinkles and folds may be formed in the nonporous region of the both side portions. Therefore, it is desirable that the holes 14 be formed throughout the whole in the width direction WD as in the illustrated embodiment. When holes are formed in the cover nonwoven fabric 13 in a manufacturing process of the diaper, a material having no holes can be used, and a hole formation site may be arbitrarily controlled. However, there are problems that introduction of hole forming equipment increases overall manufacturing, which increases burden of cost and maintenance, and adjustment of a hole shape and softness becomes difficult in a high speed line. Therefore, it is preferable to perform manufacture using a material in which holes are formed throughout the whole in the front-back direction and the width direction.

A planar shape (opening shape) of each of the holes 14 may be appropriately determined. In addition to an elongated hole shape illustrated in FIG. 17(*a*) and FIG. 17(*b*), it is possible to adopt an arbitrary shape such as a perfect circle illustrated in FIG. 17(*c*) and FIG. 17(*e*), an ellipse illustrated in FIG. 17(*d*), a polygon such as a triangle, a rectangle, a rhombus, etc., a star shape, a cloud shape, etc. Dimensions of each hole 14 are not particularly limited. However, it is preferable that a maximum dimension 14L in the front-back direction LD is set to 0.4 to 1.8 mm, particularly 0.8 to 1.3 mm, and it is preferable that a maximum dimension 14W in the width direction WD is set to 0.3 to 1.5 mm, particularly 0.5 to 1.0 mm. In a case in which the shape of the hole 14 is long in one direction as the elongated hole shape, the ellipse, the rectangle, the rhombus, etc., a maximum dimension in a longitudinal direction is preferably 2.5 times or less a maximum dimension in a direction orthogonal thereto. In addition, in a case in which the shape of the hole 14 is long in one direction, it is desirable that the longitudinal direction of the hole 14 corresponds to the front-back direction LD. However, the longitudinal direction may correspond to the width direction WD or an oblique direction.

An area and an area ratio of each hole 14 may be appropriately determined. However, the area is preferably about 0.2 to 2.5 mm$^2$ (particularly 0.5 to 1.5 mm$^2$), and the area ratio is preferably about 1.0 to 15.0% (particularly 5.0 to 10.0%).

A plane arrangement of the holes 14 can be determined as appropriate. However, a plane arrangement having regular repetition is preferable, and it is possible to adopt an arrangement in which a group of holes 14 (a group-based arrangement may be regular or irregular and may correspond to a pattern, letter shape, etc.) is regularly repeated in addition to an arrangement having regular repetition such as a rhombic lattice shape illustrated in FIG. 17(*a*), a hexagonal lattice shape illustrated in FIG. 17(*b*) (these shapes are also referred to as a staggered shape), a square lattice shape illustrated in FIG. 17(*c*), a rectangular lattice shape illustrated in FIG. 17(*d*), or a parallel body lattice illustrated in FIG. 17(*e*) (as illustrated in the figure, a mode in which two groups are provided such that groups of a large number of parallel and oblique columns intersect with each other) (including those inclined at an angle of less than 90 degrees with respect to the front-back direction LD).

Figure 17:
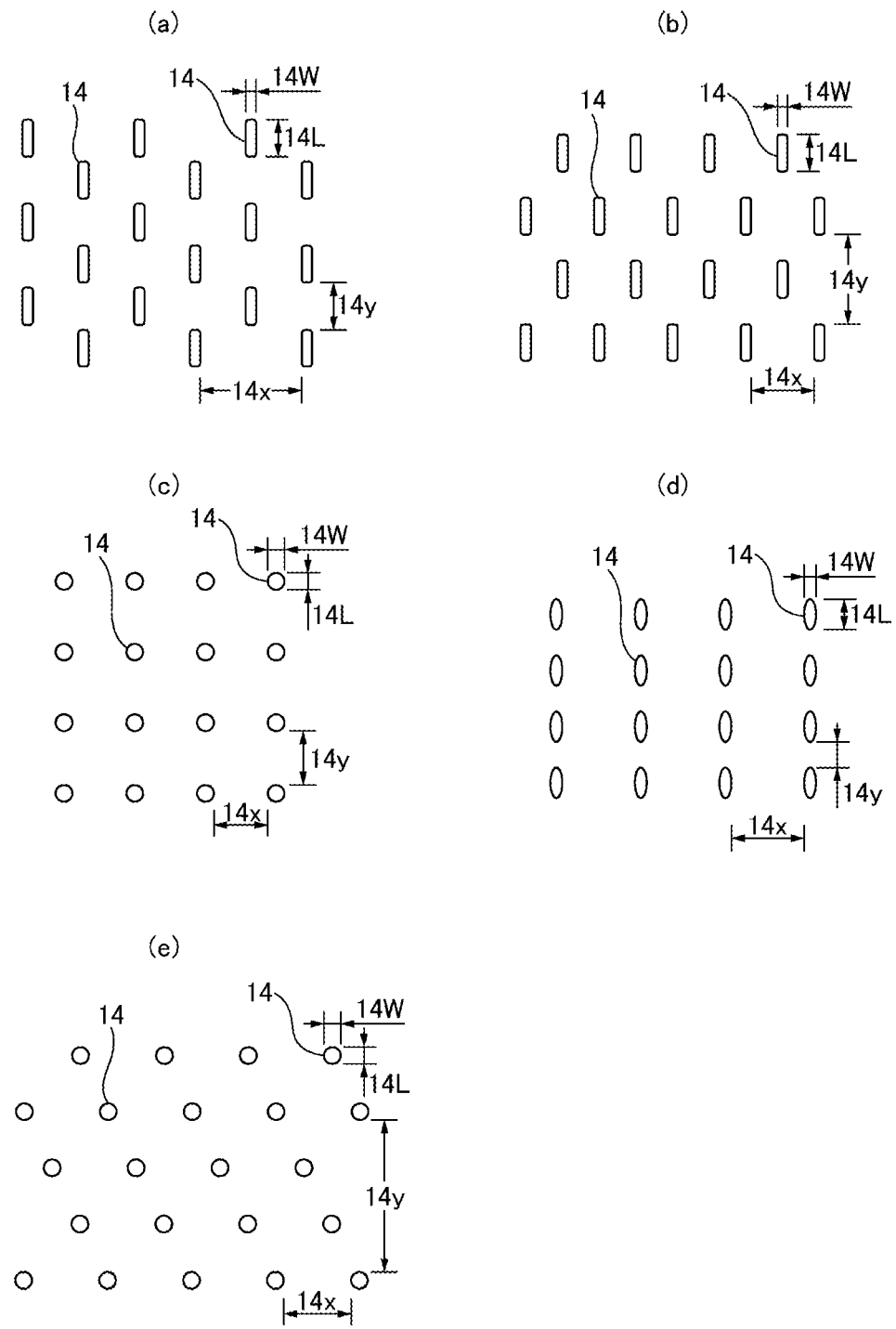
FIG. 17 is an enlarged plan view illustrating a main part of a perforated nonwoven fabric.

A front-back direction interval 14*y* and a width direction interval 14*x* of the holes 14 may be appropriately determined. However, considering air permeability, it is desirable that each of the intervals is within a range of 0.5 to 8 mm, particularly 1 to 5 mm, and it is preferable that the front-back direction interval 14*y* and the width direction interval 14*x* are averaged to be in a range of 1 to 5 mm. In particular, as illustrated in FIG. 17(*d*), when the shape of the hole 14 is set to an elongated shape in the front-back direction LD, a column of holes 14 lined up in the front-back direction at the front-back direction interval 14*y* narrower than the maximum dimension 14L of the hole 14 in the front-back direction LD is repeated at a predetermined interval in the width direction WD, and the width direction interval 14*x* thereof is wider than the maximum dimension 14L of the hole 14 in the front-back direction LD (more preferably 3 times or more the width direction dimension 14W of the hole 14), it is preferable since softness and bulkiness are not impaired while remarkably improving air permeability, and tensile strength of the sheet in the front-back direction, which is important in manufacturing, does not decrease.

Figure 14:
FIG. 14(a) is a perspective view.
FIG. 14(b) is a plan view.
FIG. 14(c) is a cross-sectional view taken along 1-1 line illustrating a hole of a perforated nonwoven fabric.
Figure 14:
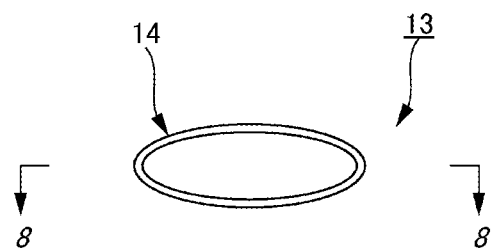
Figure 14:
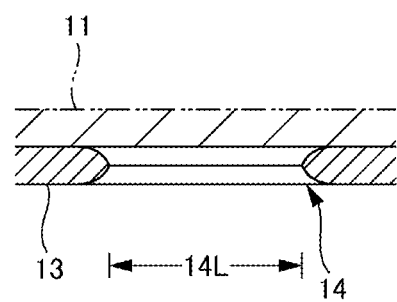
Figure 15:
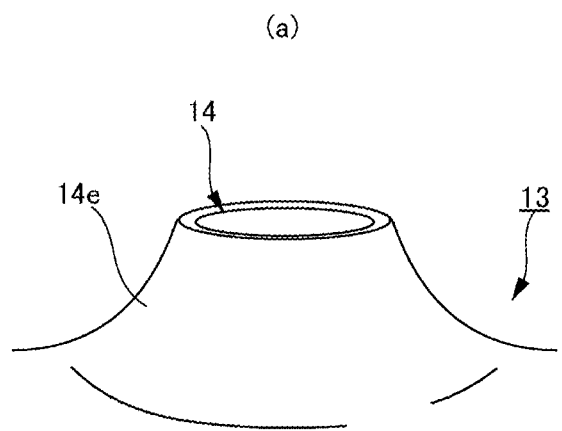
FIG. 15(a) is a perspective view.
FIG. 15(b) is a plan view.
FIG. 15(c) is a cross-sectional view taken along 1-1 line illustrating a hole of a perforated nonwoven fabric.
Figure 15:
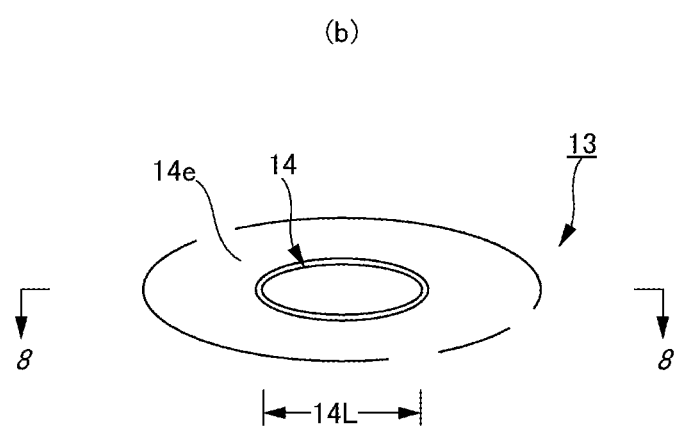
Figure 15:
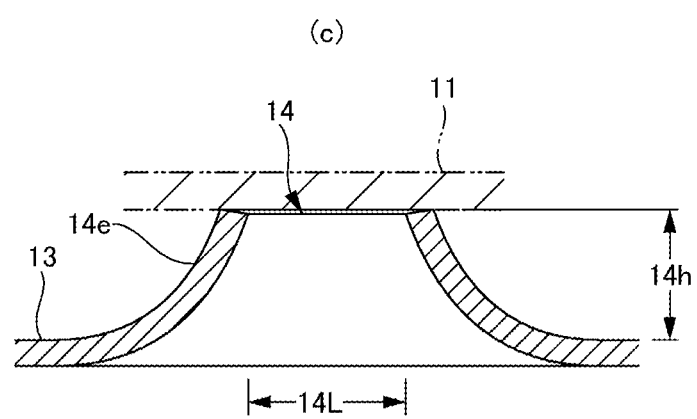
Figure 16:
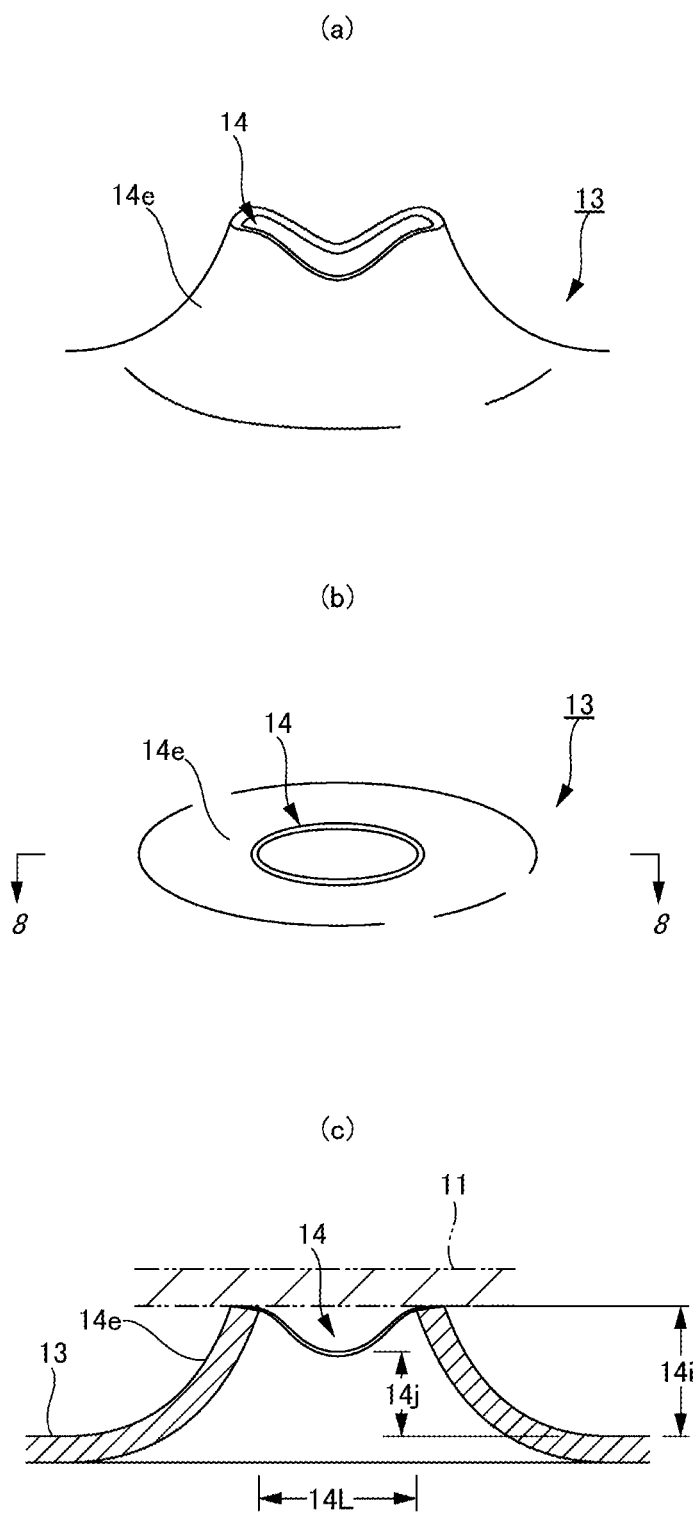
FIG. 16(a) is a perspective view.
FIG. 16(b) is a plan view.
FIG. 16(c) is a cross-sectional view taken along 1-1 line illustrating a hole of a perforated nonwoven fabric.

As a cross-sectional shape of the hole 14, it is possible to adopt any one of a first embodiment in which the thickness of the nonwoven fabric decreases from a periphery of the hole 14 toward an edge of the hole 14, and the edge of the hole 14 is located in the middle of the nonwoven fabric in the thickness direction as illustrated in FIG. 14, a second embodiment in which the peripheral portion 14e of the hole 14 is warped to the front surface side, and a warping height 14h is substantially uniform as illustrated in FIG. 15, and a third embodiment in which the peripheral portion 14e of the hole 14 is warped to the front surface side, and the peripheral portion 14e has a facing portions in which a warping height 14i is the highest and facing portions facing in a direction orthogonal thereto in which a warping height 14j is the lowest as illustrated in FIG. 16. From the viewpoint of air permeability, the second embodiment and the third embodiment in which a portion having the holes 14 is thicker than the surroundings are desirable. In particular, the third embodiment is preferable since a gap formed by a difference between the warping heights 14i and 14j of the peripheral portion 14e of the hole 14 contributes to improvement in air permeability. In the second and third embodiments, the warping heights 14g, 14h, and 14i (apparent heights measured using an optical microscope in a state no pressure is applied) are preferably about 0.2 to 1.2 mm. In the third embodiment, the highest warping height 14i is preferably about 1.1 to 1.4 times the lowest warping height 14j.

The hole 14 may correspond to a punched hole whose edge portion is formed of a cut end of a fiber or a non-punched hole (having a high fiber density in a peripheral portion) in which almost no cut end of a fiber is present at the edge portion of the hole 14 and which is formed by inserting and spreading out a pin between fibers. The former is suitable for the first embodiment, and the latter is suitable for the second embodiment and the third embodiment. For example, when the hole 14 having an elongated shape in one direction is formed by inserting a pin, a fiber of the peripheral portion 14e of the hole 14 is retracted to the outside or in the vertical direction so that the peripheral portion 14e of the hole 14 warps, and the warping height i of the facing portion of the hole 14 in the longitudinal direction becomes higher than the warping height j of the facing portion in the direction orthogonal to the longitudinal direction. In the second embodiment and the third embodiment, the edge portion of the portion in which the peripheral portion 14e of the hole 14 is warped to the surface has a lower fiber density than that of the surrounding portion in some cases. However, the fiber density is preferably the same or higher. In addition, it is desirable that fibers of the peripheral portion 14e of the hole 14 are fused to each other and may not be fused to each other.

Each of the internal surface and the external surface of the cover nonwoven fabric 13 is bonded to a facing surface through the hot melt adhesive. A fixed region of the cover nonwoven fabric 13 may be set to the whole in the front-back direction and the whole in the width direction of the cover nonwoven fabric 13, or a part may not be fixed. For example, if both end portions of the cover nonwoven fabric 13 in the width direction are not fixed, even when side portions of the absorbent body 56 are somewhat contracted due to an influence of the side gathers 60, this contraction have little effect, and wrinkles and folds are rarely formed in the cover nonwoven fabric 13, which is advantageous. A width of a non-fixing part of the both end portions of the cover nonwoven fabric 13 in the width direction in this case may be appropriately determined. For example, the width may be set to 3 to 10 mm, preferably 5 to 8 mm.

Figure 18:
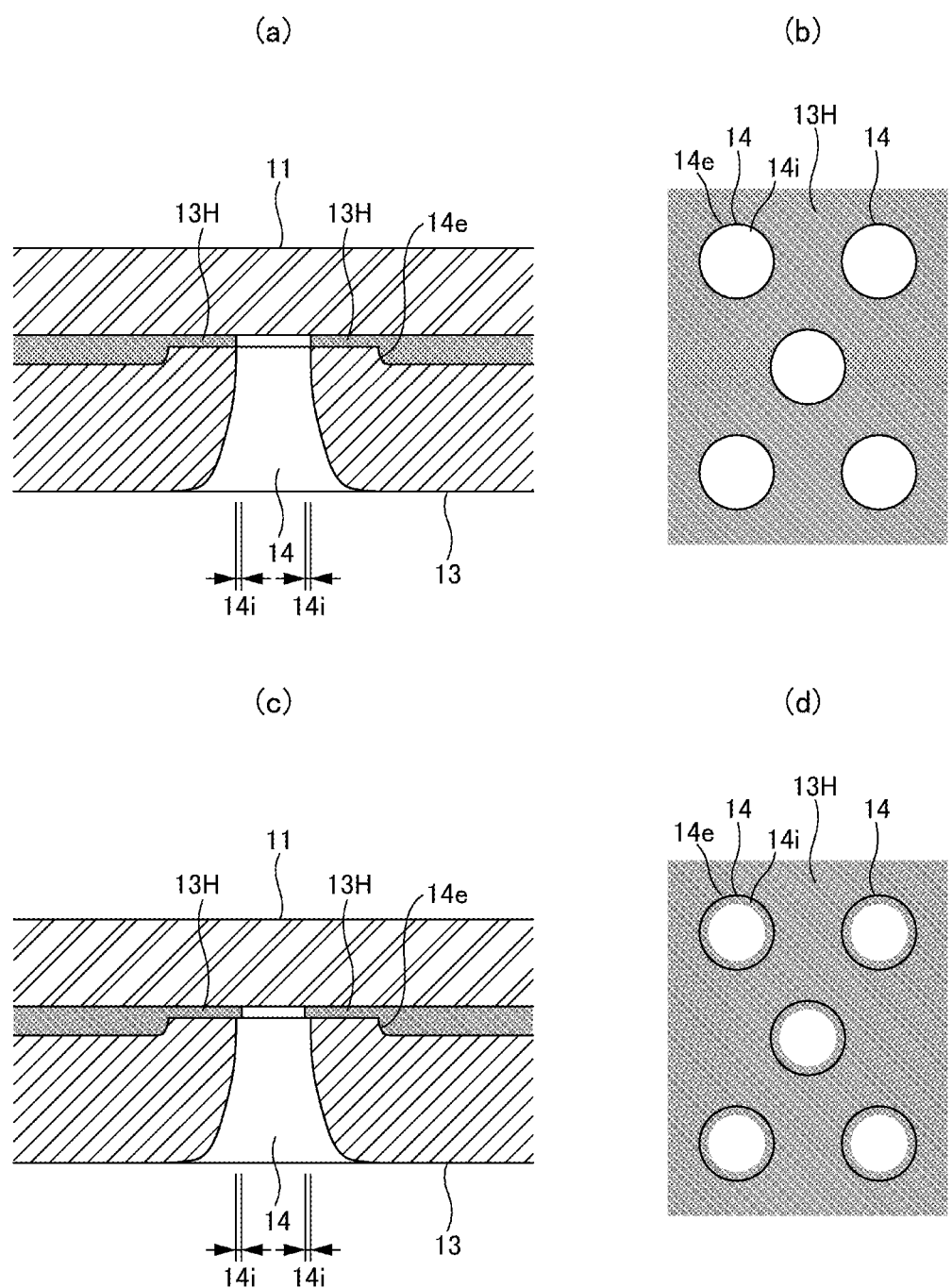
FIGS. 18(a) and 18(c) are cross-sectional views and FIGS. 18(b) and 18(d) are plan views illustrating bonded portions of a cover nonwoven fabric.

In one preferable bonding structure, as illustrated in FIG. 18, in a bonded region of at least one of the internal surface and the external surface of the cover nonwoven fabric 13, a hot melt adhesive 13H is not present on a center side of a peripheral edge portion 14i of a region overlapping the hole 14, and the hot melt adhesive 13H is applied in a continuous surface shape in a portion other than the peripheral edge portion 14i of the region overlapping the hole 14. Since the hot melt adhesive 13H is not present on the center side of the peripheral edge portion 14i of the region overlapping the hole 14, air permeability is excellent. In addition, in a portion having such a bonding structure only on a surface opposite from a surface to be touched by the skin, a sticky texture due to the hot melt adhesive 13H is rarely obtained, and the peripheral portion 14e of the hole 14 is reliably fixed to the facing surface.

Examples of a typical bonding state may include a state in which the hot melt adhesive 13H is not present in the region overlapping the hole 14, and the hot melt adhesive 13H is applied in a continuous surface shape in a region other than the region overlapping the hole 14 as illustrated in FIGS. 18(a) and 18(b), and a state in which the hot melt adhesive 13H protrudes to the peripheral edge portion 14i of the region overlapping the hole 14, the hot melt adhesive 13H is not present on the center side of the peripheral edge portion 14i of the region overlapping the hole 14, and the hot melt adhesive 13H is applied in a continuous surface shape in the portion other than the peripheral edge portion 14i of the region overlapping the hole 14 as illustrated in FIGS. 18(c) and 18(d). The former state is a particularly desirable state. Since the peripheral edge portion 14i of the region overlapping the hole 14 is a portion close to the peripheral portion 14e of the hole 14, and the cover nonwoven fabric 13 has a constant thickness, even when the hot melt adhesive 13H protrudes to this portion as in the latter, the hot melt adhesive 13H is rarely directly touched at the time of touching the surface on the opposite side from a bonded surface in the cover nonwoven fabric 13 with a hand in the portion in which only the surface on the opposite side from the surface touching the skin is bonded. A protruding width of the hot melt adhesive 13H in the peripheral edge portion 14i of the region overlapping with the hole 14 is less than or equal to a half of the thickness of the cover nonwoven fabric 13 and preferably about 0.5 mm or less. In addition, it is desirable that the hot melt adhesive 13H is not present in a portion of 80% or more of the area of the region overlapping the hole 14.

The cross-sectional shape of the hole 14 in the cover nonwoven fabric 13 is not limited. However, when the peripheral portion 14e of the hole 14 corresponds to the warped portion warped to the liquid impervious sheet 11 side as described above, a hole diameter viewed from the liquid impervious sheet 11 side becomes smaller than a hole diameter viewed from a surface on the opposite side from the liquid impervious sheet 11 side. Therefore, in a portion in which only the surface on the opposite side from the surface touching the skin is bonded, the hot melt adhesive 13H is rarely directly touched at the time of touching the surface on the opposite side from the bonded surface with the hand. In addition, the warped portion supports the cover nonwoven fabric 13 with respect to the facing surface as a post, and thus is bulky and excellent in air permeability when compared to a non-porous nonwoven fabric having the same basis weight. Further, in a region other than the peripheral portion 14e of the hole 14, bonding of the cover nonwoven fabric 13 and the liquid impervious sheet 11 is likely to float (even though the hot melt adhesive 13H fills a space between sheets without any gap in FIG. 18, an actual coating amount is small, and a gap is liable to be formed), and thus the peripheral portion 14e of the hole 14 is reliably bonded while bonding is incomplete in other regions (an actual bonded area becomes small). In this way, it is possible to obtain excellent softness/fullness.

Figure 19:
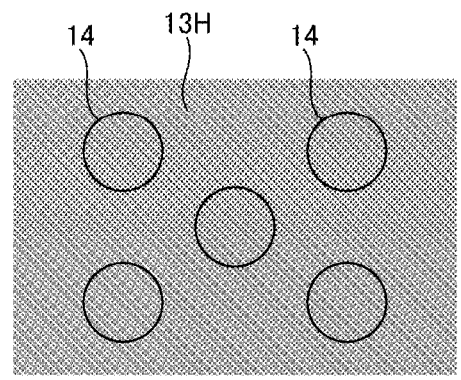
FIG. 19 is a plan view illustrating a change during application of a hot melt adhesive.
Figure 19:
Figure 19:
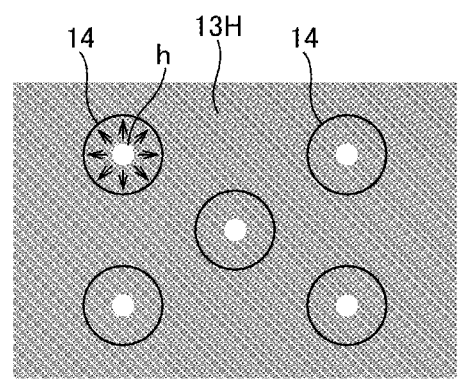
Figure 19:
Figure 19:
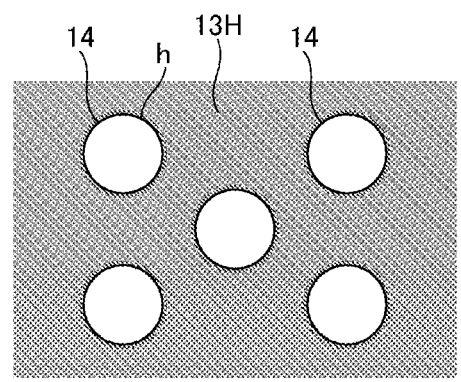

Such a bonding structure can be produced by applying the hot melt adhesive to the bonding surface in the perforated nonwoven fabric in a continuous surface shape without using air, and bonding facing surfaces. This scheme is based on a new finding in which when the hot melt adhesive is applied to the bonding surface in the perforated nonwoven fabric in a continuous surface shape without using air, an opening (hole) h is formed at a center of a portion overlapping a hole of the perforated nonwoven fabric in the hot melt adhesive due to surface tension of the hot melt adhesive before bonding to the facing surface, and the opening widens to the peripheral portion of the hole of the perforated nonwoven fabric. That is, when such a bonding scheme is adopted, an opening (hole) is formed at a center of a portion overlapping the hole 14 of the perforated nonwoven fabric in the hot melt adhesive 13H due to surface tension of the hot melt adhesive 13H before bonding to a target member and after the hot melt adhesive 13H is applied to the perforated nonwoven fabric in a continuous surface shape as illustrating changes using arrows in FIG. 19, and the opening h widens to the peripheral portion 14e of the hole 14 of the perforated nonwoven fabric. Therefore, after the perforated nonwoven fabric is bonded to the target member, the hot melt adhesive 13H is not present in a most part of the hole 14 as in an example illustrated in FIG. 18, and the hot melt adhesive 13H does not escape or exude from the hole 14 by air. Thus, the sticky texture is rarely obtained when the surface on the opposite side from the bonded surface is touched with hand.

As a hot melt applicator that applies the hot melt adhesive in a continuous surface shape without using air, it is possible to suitably use slot coat that brings a coating head (die) into contact with the bonding surface of the perforated nonwoven fabric and extrudes the hot melt adhesive from a slit extending along a cross direction (CD) (a direction orthogonal to a machine direction (MD) (a flow direction of a production line)) provided at a tip of the coating head to perform coating, or non-contact type slot coat that extrudes the hot melt adhesive from the slit extending along the CD provided at the tip of the coating head in a state in which the coating head (die) floats from the bonded surface of the perforated nonwoven fabric, and stretches and applies the hot melt adhesive in a form of an extremely thin film by a difference with a transporting speed of the perforated nonwoven fabric.

Bonding conditions may be appropriately determined. However, to promptly move the hot melt adhesive 13H overlapping the hole 14 to the peripheral portion 14e of the hole 14, and firmly bond the peripheral portion 14e of the hole 14, it is desirable to satisfy at least one of the following conditions.

Melt viscosity of hot melt adhesive (temperature 140° C.): 3,000 to 2,600 mPa·s

Melt viscosity of hot melt adhesive (temperature 160° C.): 1,150 to 1,550 mPa·s

Temperature during application of hot melt adhesive to perforated nonwoven fabric: 110 to 150° C.

Coating amount of hot melt adhesive to perforated nonwoven fabric: 1.0 to 8.0 g/m²

Open time after application of hot melt adhesive: 0.1 to 1.0 second

Figure 20:
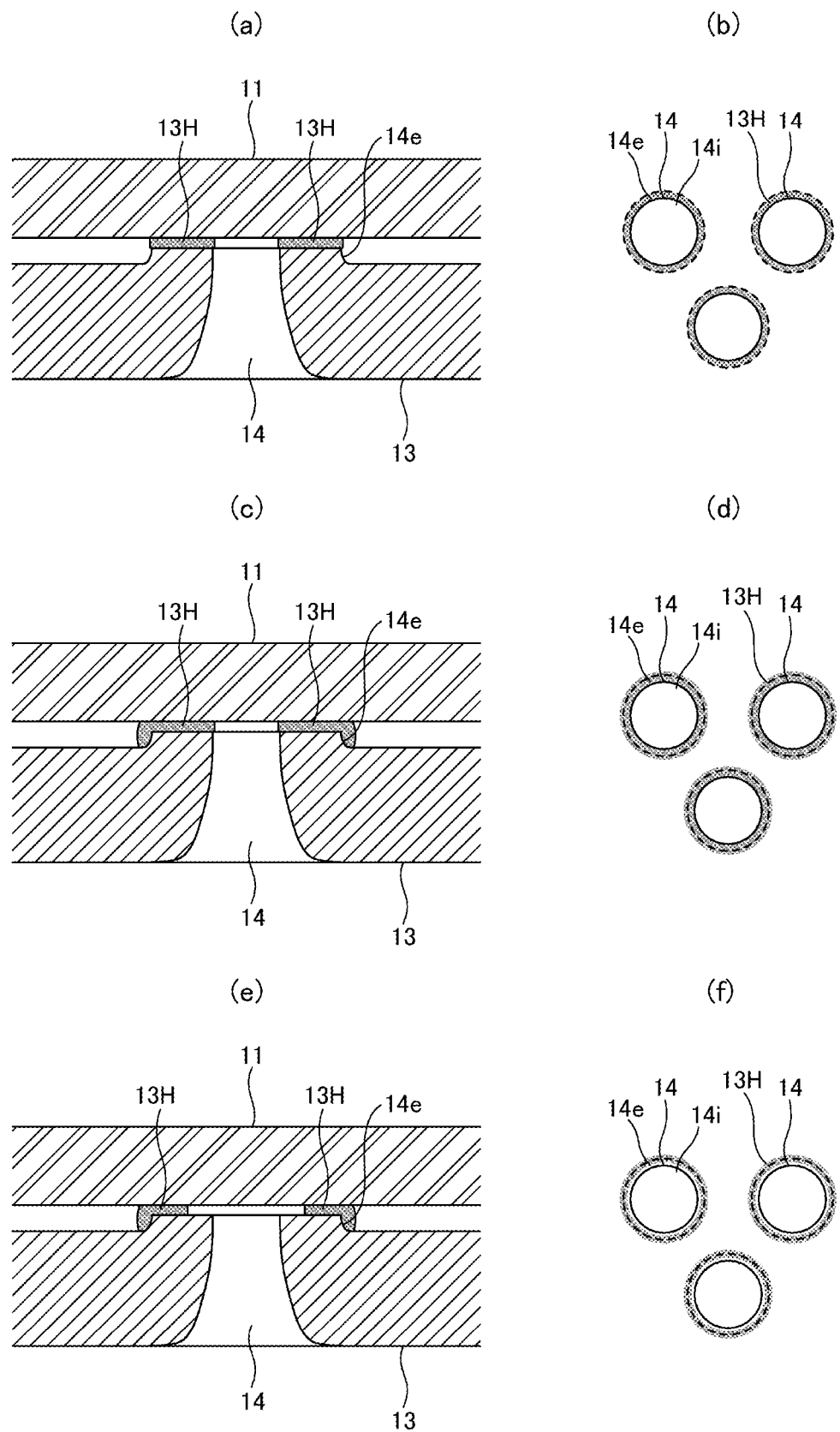
FIGS. 20(a), 20(c), and 20(e) are cross-sectional views
FIGS. 20(b), 20(d), and 20(f) are plan views illustrating bonded portions of the cover nonwoven fabric.

In another preferable bonding structure, as illustrated in FIG. 20, the peripheral portion 14e of the hole 14 in the cover nonwoven fabric 13 corresponds to a warped portion which is warped, at least the tip portion of the warped portion corresponds to a bonded portion stuck to the facing surface (in this case, the liquid impervious sheet 11) through the hot melt adhesive 13H, and a portion other than this bonded portion is not bonded. When such a bonding structure is adopted, the bonded area decreases, and thus flexibility is not impaired, and the peripheral portion 14e of the hole 14 is reliably fixed to the facing surface. In particular, the warped portion supports the cover nonwoven fabric 13 with respect to the facing surface as a post, and thus is bulky and excellent in air permeability when compared to a non-porous nonwoven fabric having the same basis weight.

Examples of a typical bonding state may include a state in which only the tip portion of the warped portion is bonded to the facing surface through the hot melt adhesive 13H as illustrated in FIGS. 20(a) and 20(b), a state in which the entire warped portion is bonded to the facing surface through the hot melt adhesive 13H as illustrated in FIGS. 20(c) and 20(d), and a state in which an entire outside of an internal portion of the tip portion in the warped portion is bonded to the facing surface through the hot melt adhesive 13H and the internal portion of the tip portion is not bonded as illustrated in FIGS. 20(e) and 20(f). Even though it is desirable that no adhesive is present on an inner peripheral surface of the hole 14 of the warped portion and the site of the facing surface overlapping the hole 14, an adhesive may somewhat protrude.

A bonding state of the warped portion is not limited to the illustrated embodiment as long as at least the tip portion is stuck to the facing surface through the hot melt adhesive 13H, and at least a part of the hole 14 in a circumferential direction may corresponding to any one of the above bonding states. For example, as in the embodiment illustrated in FIG. 15 and FIG. 16, when the warped portion has a cylindrical shape continuously in the circumferential direction of the hole 14, the entire tip portion of the cylindrical shape in the circumferential direction is preferably in a bonding state. However, a part thereof may be in another bonding state or may not be bonded. In addition, when the warped portion is formed only in a part of the hole 14 in the circumferential direction, it suffices that a tip portion of the part is in the bonding state. Further, different bonding states may coexist in a large number of warped portions.

(Inner and Outer Joined Portion)

The inner member 200 may be fixed to the outer members 12F and 12B by bonding means based on material welding such as heat sealing or ultrasonic sealing or a hot melt adhesive. In the illustrated embodiment, the inner member 200 is fixed to the internal surfaces of the outer members 12F and 12B through the back surface of the inner member 200, that is, the back surface of the liquid impervious sheet 11 in this case, and the hot melt adhesive applied to the root portion 65 of the side gather 60. The inner and outer joined portions 201 and 202 that fix the inner member 200 and the outer members 12F and 12B to each other may be provided almost entirely in a region in which the members overlap with each other, and may be provided, for example, in a portion excluding both end portions of the inner member 200 in the width direction. In particular, when the inner and outer joined portions 201 and 202 are provided over a region overlapping the cover nonwoven fabric 13 and a region on both width sides of this region, it is possible to firmly fix the both side portions of the cover nonwoven fabric 13, and the both side portions of the cover nonwoven fabric 13 are less likely to be peeled off from the inner member 200, which is preferable.

Figure 9:
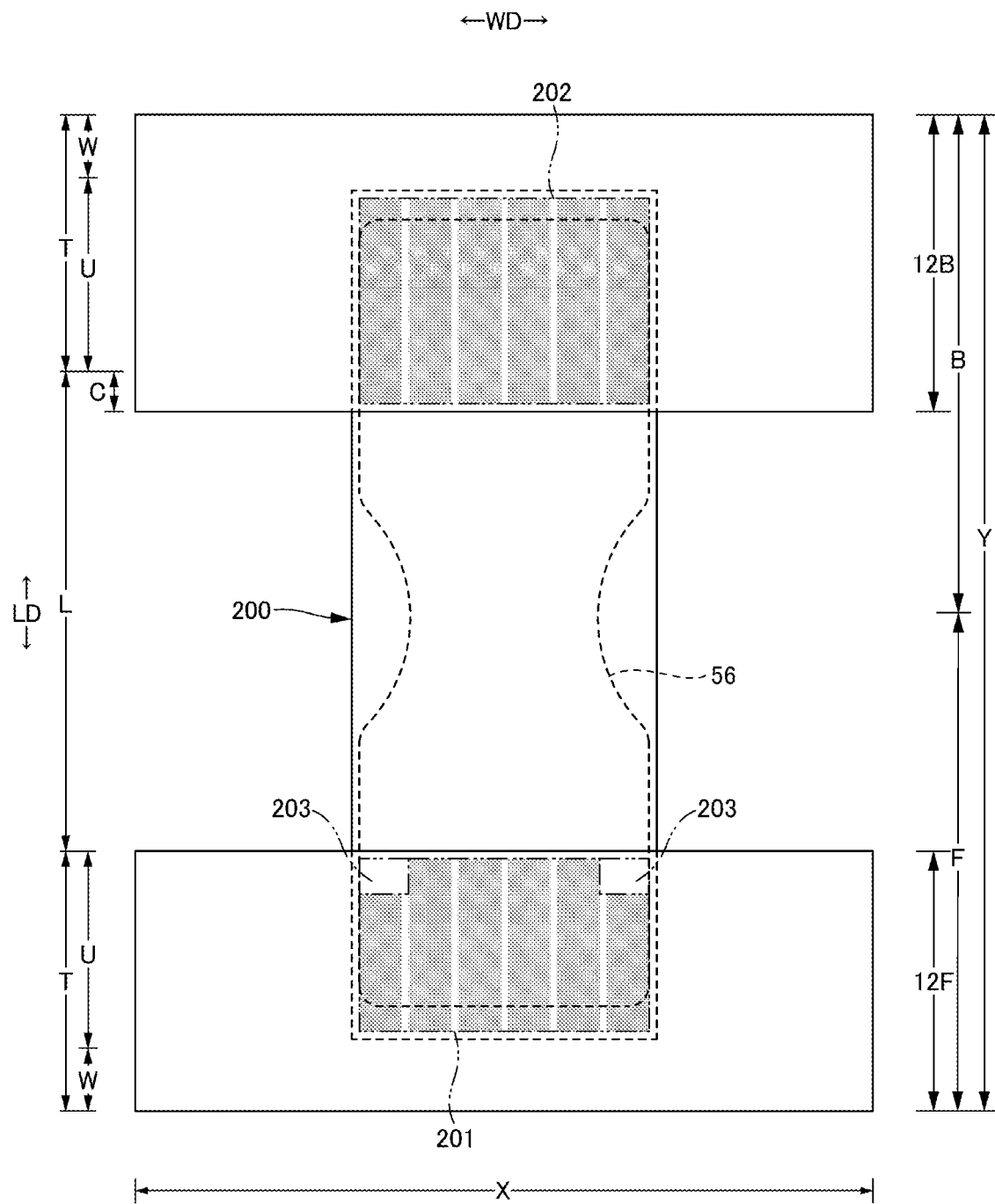
FIG. 9 is a plan view illustrating only a main part of the external surface of the underpants-type disposable diaper in the spread state.

As illustrated in FIG. 9 and FIG. 10, it is preferable that the inner and outer joined portion 201 of the front side outer member 12F is provided to extend over both end portions in the width direction on the waist side, a width thereof decreases stepwise or continuously toward a crotch-side edge of the front side outer member 12F, and a non-joined part 203 is formed on both end portions of the crotch side of the front side outer member 12F in the width direction. In this way, even in an outer member separated type in which the crotch-side edge of the front side outer member 12F intersects the side edge of the inner member 200 at the right angle or an angle close thereto in a linear shape along the width direction or a shape close thereto, fitting of the inguinal region in a sitting position or during walking is improved.

Dimensions of the non-joined part 203 may be appropriately determined. However, in the case of use for infants, a front-back direction dimension may be set to about 10 to 30 mm, and a width direction dimension may be set to about 10 to 25 mm. It is preferable that a front edge of the non-joined part 203 (a site located closest to the front side in the case of a curve) is located at the back side portion of the front side half fallen part 68F.

In particular, when the elastic member in the stretchable region A2 at the lower waist portion of the front side outer member 12F extends to the inside of the non-joined part 203 formed at both end portions of the crotch side of the front side outer member 12F in the width direction, fitting of the inguinal region is more preferable. In addition, when the bending is adopted as the side gather 60 of the first embodiment described above, and the front side half fallen part 68F is provided, fitting of the inguinal region is further improved. Further, it is more preferable that the front side half fallen part 68F is the same as the crotch side edge of the front side outer member 12F or extends further to the center side in the front-back direction as described above. Further, in a case in which the absorbent body 56 has an hourglass shape, when the front side half fallen part 68F is located on the absorbent body without overlapping the narrower portion 56N, a root of the three-dimensional gather is stabilized, and the front side half fallen part 68F is easy to stand, which is preferable.

Meanwhile, when inner and outer joined portions 202 of the back side outer member 12B are provided to extend over both end portions in the width direction over the whole in the front-back direction, the inner member 200 rarely bites into the intergluteal cleft, which is preferable. In this case, when the bending mode is adopted as the side gathers 60 of the first embodiment described above, and the back side half fallen part 68B is provided, the tip side part 60A of the three-dimensional gather rarely falls in the opposite direction due to an inclination toward the intergluteal cleft, which is preferable. Further, as described above, when the back side half fallen part 68B is the same as the front edge of the back side outer member 12B or extends to the center side in the front-back direction LD, prevention of biting of the inner member 200 into the intergluteal cleft is further improved, the gluteal cover portion C is rarely shifted in the case of including the gluteal cover portion C, and ability to maintain covering of the gluteal region becomes excellent. It is more preferable that a front-back direction length of the back side half fallen part 68B is longer than a front-back direction length of the back side fallen part 67. Further, in a case in which the absorbent body 56 has the hourglass shape, when the back side half fallen part 68B is located on the absorbent body without overlapping the narrower portion 56N, in particular, the inner member 200 rarely bites into the intergluteal cleft, which is preferable.

In the case of adopting the bending mode as the side gather 60 of the first embodiment, when both the front side half fallen part 68F and the back side half fallen part 68B are provided, and a length of the back side half fallen part 68B with respect to a length of the front side half fallen part 68F is in a range of 0.9 to 1.5, the three-dimensional gather can stand long and high, and each of the tip side part 60A and the root side part 60B is not excessively free. Thus, fitting of the entire periphery of the leg becomes excellent.

Description of Terms in Specification

Terms below in the specification have meanings below unless otherwise specified in the specification.

The "front-back (longitudinal) direction" refers to a direction connecting a ventral side (front side) and a dorsal side (back side), and the "width direction" refers to a direction (left-right direction) orthogonal to the front-back direction.

The "front surface side" refers to a side close to the skin of the wearer when the underpants-type disposable diaper is worn, and the "back surface side" refers to a side far from the skin of the wearer when the underpants-type disposable diaper.

The "front surface" refers to a surface of the member on the side close to the skin of the wearer when the underpants-type disposable diaper is worn, and the "back surface" refers to a surface of the member on the side far from the skin of the wearer when the underpants-type disposable diaper.

The "area ratio" refers to an area of a ratio of a target portion to a unit area, and is expressed as a percentage by dividing a total area of target portions (for example, holes) in a target region (for example, the cover nonwoven fabric) by an area of the target region. In an embodiment in which a plurality of target portions is provided at intervals, it is desirable to set a target region having a size such that ten or more target portions are included and obtain an area ratio. For example, the area ratio of the holes can be measured by the following procedure, for example, using the product name VHX-1000 manufactured by KEYENCE Corporation, under the measurement conditions of 20 times.

(1) Setting on a 20 times lens is performed, and a focus is adjusted. A position of a nonwoven fabric is adjusted so that 4×6 holes enter.

(2) Brightness of a region of the holes is specified, and an area of the holes is measured.

(3) Color extraction of "area measurement" in "measurement/comment" is clicked on. A hole part is clicked on.

(4) "Batch measurement" is clicked on, "display measurement result window" is checked, and saving as "CSV data" is performed.

The "stretch rate" refers to a value when the natural length is set to 100%.

The "gel strength" is measured as follows. 1.0 g of a super absorbent polymer is added to 49.0 g of artificial urine (mixture of urea: 2 wt %, sodium chloride: 0.8 wt %, calcium chloride dihydrate: 0.03 wt %, magnesium sulfate heptahydrate: 0.08 wt %, and ion exchanged water: 97.09 wt %) and stirred using a stirrer. After the produced gel is left in a temperature and humidity testing chamber of 40° C.×60% RH for three hours, the temperature is returned to room temperature, and gel strength is measured using a card meter (Curdmeter-MAX ME-500, manufactured by I. Techno Engineering Co., Ltd.).

The "basis weight" is set as below. A sample or a specimen is pre-dried, and then is left in a test room or a device in a standard state (temperature 20±5° C., relative humidity 65% or less in a test location), and is put in a constant weight state. Pre-drying refers to setting the weight of the sample or the specimen to a constant weight in an environment in which relative humidity is in a range of 10 to 25% and temperature does not exceed 50° C. Pre-drying is unnecessary for a fiber having an official moisture regain of 0.0%. A sample having dimensions of 200 mm×250 mm (±2 mm) is cut off from the specimen in the constant weight state using a sampling template (200 mm×250 mm, ±2 mm). A weight of the sample is measured and multiplied by 20 to calculate a weight per square meter, and the weight is set to the basis weight.

A "thickness" is automatically measured using an automatic thickness measurement apparatus (KES-G5 handy compression measurement program) under the condition of a load of 0.098 N/cm$^2$ and a pressurized area of 2 cm$^2$.

The "water absorption capacity" is measured by JIS K7223-1996 "water absorption capacity test method for superabsorbent resin".

The "water absorption rate" is set to a "time to an end point" when JIS K7224-1996 "water absorption rate test method for super absorbent resin" is performed using 2 g of super absorbent polymers and 50 g of physiological saline.

The "spread state" refers to a flatly spread state without contraction or slack.

Dimensions of each portion refer to dimensions in a spread state rather than a natural length state unless otherwise stated.

When there is no description about an environmental condition in a test or measurement, it is presumed that the test or measurement is performed in a test room or a device in a standard state (temperature 20±5° C., relative humidity 65% or less in a test location).

INDUSTRIAL APPLICABILITY

The invention may be used for an underpants-type disposable diaper.

REFERENCE SIGNS LIST 11 liquid impervious sheet
12A side seal portion
12B back side outer member
12E waist extended section
12F front side outer member
12H inner sheet layer
12S outer sheet layer
13 cover nonwoven fabric
14 hole
17 waist portion elastic member
18 unnecessary elastic member
200 inner member
201, 202 inner and outer joined portions
203 non-joined part
25 display sheet
30 top sheet
40 intermediate sheet
50 absorbent element
56 absorbent body
58 package sheet
60 side gather
60A tip side part
60B root side part
62 gather nonwoven fabric
67 fallen part
68B back side half fallen part
68F front side half fallen part
A1 non-stretchable region
A2 stretchable region
C gluteal cover portion
L intermediate region
LD front-back direction
T lower torso
U lower waist portion
W waist portion
WD width direction
WO waist opening

The invention claimed is:

1. An underpants-type disposable diaper comprising:
a front side outer member configuring at least a lower torso portion of a front body and a back side outer member configuring at least a lower torso portion of a back body, the front side outer member and the back side outer member being separated from each other and spaced apart in a front-back direction in a middle in the front-back direction;
an inner member including a liquid pervious top sheet located on a front surface side, a liquid impervious sheet formed of a resin film located on a back surface side, and an absorbent body interposed therebetween, extending in the front-back direction from the front side outer member to the back side outer member and being joined to each of the front side outer member and the back side outer member, a waist opening and a pair of left and right leg openings being formed by joining both side portions of the front side outer member and both side portions of the back side outer member, respectively; and
a display sheet formed of a resin film and being provided between at least one of the front side outer member and the back side outer member and the inner member,
wherein a perforated nonwoven fabric provided with a plurality of holes having intervals and penetrating a front and a back is interposed at least from a crotch side edge of the at least one of the front side outer member and the back side outer member overlapping the display sheet, toward a side of the waist opening, to a region between the display sheet and the liquid impervious sheet, and
wherein an internal surface and an external surface of the perforated nonwoven fabric are bonded to facing surfaces, respectively, through a hot melt adhesive; and
wherein, in a bonding region on at least one of the internal and external surfaces of the perforated nonwoven fabric, the hot melt adhesive is not present inward of a peripheral portion of an area corresponding to each hole, and the hot melt adhesive is present in a continuous plane in and outwards of the peripheral portion of the area corresponding to each hole.

2. The underpants-type disposable diaper according to claim 1, wherein
the perforated nonwoven fabric is a cover nonwoven fabric which extends from a region between the front side outer member and the inner member to a region between the back side outer member and the inner member, and covers a back surface of the inner member in a site in which the front side outer member and the back side outer member are spaced apart.

3. The underpants-type disposable diaper according to claim 2, further comprising side gathers extending from both side portions of the inner member to come into contact with peripheries of legs of a wearer, wherein each of the side gathers has a base at a side portion of the inner member on a back surface side of the liquid impervious sheet and has a gather nonwoven fabric forming an external surface at least from the base to a tip, and the perforated nonwoven fabric extends from a region between a base portion of at least one of the side gathers and the liquid impervious sheet to a region between a base portion of the other one of the side gathers and the liquid impervious sheet.

4. The underpants-type disposable diaper according to claim 1, wherein an inner and outer joined portion that joins the inner member and the at least one of the front side outer member and the back side outer member overlapping the perforated nonwoven fabric is provided over a region overlapping the perforated nonwoven fabric and a region on both width-direction sides beyond the overlapping region.

5. An underpants-type disposable diaper comprising:

a front side outer member configuring at least a lower torso portion of a front body and a back side outer member configuring at least a lower torso portion of a back body, the front side outer member and the back side outer member being separated from each other and spaced apart in a front-back direction in a middle in the front-back direction;

an inner member including a liquid pervious top sheet located on a front surface side, a liquid impervious sheet formed of a resin film located on a back surface side, and an absorbent body interposed therebetween, extending in the front-back direction from the front side outer member to the back side outer member and being joined to each of the front side outer member and the back side outer member, a waist opening and a pair of left and right leg openings being formed by joining both side portions of the front side outer member and both side portions of the back side outer member, respectively; and a display sheet formed of a resin film and being provided between at least one of the front side outer member and the back side outer member and the inner member;

wherein a perforated nonwoven fabric provided with a plurality of holes having intervals and penetrating a front and a back is interposed at least from a crotch side edge of the at least one of the front side outer member and the back side outer member overlapping the display sheet, toward a side of the waist opening, to a region between the display sheet and the liquid impervious sheet;

wherein an internal surface and an external surface of the perforated nonwoven fabric are bonded to facing surfaces, respectively, through a hot melt adhesive;

wherein an area around each hole in the perforated nonwoven fabric is warped toward the liquid impervious sheet to form a warped portion;

wherein at least a tip portion of the warped portion in the perforated nonwoven fabric has a bonded portion stuck to a facing surface on the side of the liquid impervious sheet through the hot melt adhesive; and wherein a portion other than the bonded portion in the perforated nonwoven fabric is not bonded to the facing surface on the side of the liquid impervious sheet.

6. The underpants-type disposable diaper according to claim 2, wherein an inner and outer joined portion that joins the inner member and the outer member overlapping the perforated nonwoven fabric is provided over a region overlapping the perforated nonwoven fabric and a region on both width-direction sides beyond the overlapping region.

7. The underpants-type disposable diaper according to claim 3, wherein an inner and outer joined portion that joins the inner member and the outer member overlapping the perforated nonwoven fabric is provided over a region overlapping the perforated nonwoven fabric and a region on both width-direction sides beyond the overlapping region.

\* \* \* \* \*